(12) United States Patent
Kosaka et al.

(10) Patent No.: US 6,640,127 B1
(45) Date of Patent: Oct. 28, 2003

(54) SURGICAL OPERATION NAVIGATING SYSTEM USING A REFERENCE FRAME

(75) Inventors: Akio Kosaka, Hachioji (JP); Takao Shibasaki, Tokyo (JP); Akito Saito, Hino (JP); Takeo Asano, Kunitachi (JP); Hiroshi Matsuzaki, Hachioji (JP); Yukihito Furuhashi, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 131 days.

(21) Appl. No.: 09/590,466

(22) Filed: Jun. 9, 2000

(30) Foreign Application Priority Data

Jun. 10, 1999 (JP) ............................................. 11-163962
Sep. 27, 1999 (JP) ............................................. 11-273067

(51) Int. Cl.$^7$ ................................................. A61B 5/05
(52) U.S. Cl. ........................ 600/426; 600/429; 600/414; 600/417; 606/130
(58) Field of Search ........................ 600/407, 410, 600/411, 425, 427, 417, 414, 426, 429, 476, 473; 382/128, 131; 606/130

(56) References Cited

U.S. PATENT DOCUMENTS

| | | | | |
|---|---|---|---|---|
| 5,871,445 A | * | 2/1999 | Bucholz | 600/407 |
| 6,165,181 A | * | 12/2000 | Heilbrun et al. | 600/407 |
| 6,246,900 B1 | * | 6/2001 | Cosman et al. | 600/426 |
| 6,259,942 B1 | * | 7/2001 | Westermann et al. | 378/162 |
| 6,347,240 B1 | * | 2/2002 | Foley et al. | 600/426 |

FOREIGN PATENT DOCUMENTS

| | | |
|---|---|---|
| JP | 7-311834 | 11/1995 |

OTHER PUBLICATIONS

R.H. Taylor, et al., "Computer–Integrated Surgery", Technology and Clinical Applications, The MIT Press, pp. 319–341, 1996.

N. Hata, et al., "Development of a Frameless and Armless Stereotactic Neuronavigation System with Ultrasonographic Registration", Neurosurgery, vol. 41, No. 3, pp. 608–614, Sep. 1997.

R.Y. Tsai, "A Versatile Camera Calibration Technique for High–Accuracy 3D Machine Vision Metrology Using Off–the–Shelf TV Cameras and Lenses", IEEE Journal of Robotics and Automation, vol. 3, No. 4, pp. 323–344, Aug. 1987.

B.K.P. Horn, "Closed–form solution of absolute orientation using unit quaternions", Journal of Optical Society of America A, vol. 4, pp. 629–642, Apr. 1987.

* cited by examiner

Primary Examiner—Marvin M. Lateef
Assistant Examiner—Jeoyuh Lin
(74) Attorney, Agent, or Firm—Scully, Scott, Murphy & Presser

(57) ABSTRACT

A reference frame adapted to be fitted to a subject of medical treatment and provided with markers for determining the position or the orientation of the subject comprises fitting section for fitting the reference frame with the subject at least three spots (tops of the left and right ears and the nasal projection) along the undulations of the surface thereof and three or more than three markers detectable at least ether in an X-ray image or in an MRI image of the reference frame, the markers being to be arranged at predetermined positions not connectable by a straight line. A surgical operation navigating system determines the coordinates of the markers in a coordinate system defined for the image taken for the purpose of medical examination of the subject who is carrying the reference frame on the basis of the obtained image. Then the corresponding relationship is established between the coordinate system for the image for examination and the coordinate system for the real space containing the markers on the basis of the result of the operation of determining the coordinates of the markers in the coordinate system for the image for examination and the coordinates of the markers in the coordinate system for the real space.

44 Claims, 17 Drawing Sheets

SURGICAL OPERATION NAVIGATING SYSTEM USING A REFERENCE FRAME

CROSS-REFERENCE TO RELATED APPLICATIONS

This application claims benefit of Japanese Applications No. 11-163962, filed on Jun. 10, 1999; and No. 11-273067, filed on Sep. 27, 1999, the contents of which are incorporated by this reference.

BACKGROUND OF THE INVENTION

This invention relates to a reference frame to be suitably used for surgical operations including those of brain surgery and also to a marker to be used with such a reference frame. The present invention also relates to a surgical operation navigating system using such a reference frame.

In the field of surgical operations including those of brain surgery, it is highly important to accurately determine the positional relationship between the target portion of the patient for surgery and the surgical instrument to be used for the operation through measurement. It is also important to establish the positional correspondence between the target portion of the patient and an image of the target portion obtained for examination. The operation of defining the positional relationship between the target portion of the patient and the surgical instrument and also that of defining the positional relationship between the target portion of the patient and an image of the target portion are referred to as operative calibration. Known techniques for operative calibration include the one proposed in R. H. Taylor (ed.), "Computer-Integrated Surgery", MIT Press, 1996 (hereinafter referred to as Document 1) that utilizes a stationary frame.

N. Hata, et. al, "Development of a frameless and armless stereotactic neuronavigation system with ultrasonographic registration", Nueorsurgery, Vol. 41, No. 3, September 1997, pp. 609-614 (hereinafter referred to as Document 2) describes the use of a specifically designed reference frame fitted to the patient and used to register the coordinates representing the target portion of the patient and an image of the target portion obtained for examination.

The technique described in Document 1 utilizes a stationary metal frame, by means of which a metal marker is driven into the body of the patient from the body surface like a screw for the purpose of fixing and registration. In other words, this technique is highly invasive to the body of the patient.

According to Document 2, the reference frame is made of acrylic resin and held stationary to the body of the patient by way of the left auditory tube and the nasal projection and a total of four metal cubes are fitted onto the reference frame and used as markers.

Then, the left auditory tube and the nasal projection are made rigid by means of silicone rubber.

Thereafter, the markers are located in a CT image and actually detected by means of a probe on the body of the patient. In actual operation scenes, the doctor carries out the operation while watching the markers as detected by an ultrasonic wave.

However, the method described in Document 2 are accompanied by the following problems.

1) The accuracy of registration using the reference frame is rather poor because the frame is anchored to the body of the patient at two positions to make it held stationary.

2) Once the reference frame is removed from the body of the patient, it is difficult to accurately restore the original posture of the frame because it is anchored to the body of the patient by silicone rubber.

3) The markers cannot be used in an MRI image because they are made of metal.

4) The images of the markers can vary enormously depending on the view angle and hence it is highly difficult to define a position to be probed and the corresponding position in the image obtained for examination because the metal markers have a cubic profile.

5) It is difficult to conduct the surgical operation while leaving the reference frame on the patient and it is also difficult to put a drape on the frame in order to maintain the clean environment of the operation because the frame is large due to its intrinsic structure.

Meanwhile, Japanese Patent Application KOKAI Publication No. 7-311834 proposes an auxiliary device adapted to register images obtained for different examinations by using a reference frame that is a sort of mouthpiece reflecting the impression of the teeth of the patient.

However, the frame as described in the above KOKAI Publication is designed to register images obtained for different examinations and hence cannot suitably be m used for actual surgical operations. For example, a connector that looks like an antenna is used and arranged between the mouthpiece and the forehead of the patient and the markers are put to the front end of the connector so that it is not possible to put a drape on the frame for the surgical operation. In the case of a surgical operation using an endoscope inserted into the body through one of the nostrils of the patient that is attracting attention recently, the connector arranged at the center of the face of the patient obstructs the endoscope trying to enter the body through the nostril. Additionally, the markers are located at upper positions of the mouthpiece. In other words, they are arranged around the oral cavity. Additionally, a total of three markers are arranged on a horizontal plane on the head at the cost of accuracy of registration particularly when images of the brain are taken for brain surgery at a position right above the head. Still additionally, since an upper portion and a central portion of the brain are not covered by the markers, a relatively large error can become involved when computationally determining the coordinate transformation parameters necessary for the registration of an upper portion and an central portion of the head even if the markers can be detected in the images obtained for examination.

Furthermore, in actual operation scenes, there are cases it is impossible to observe the markers on the reference frame in a real space. Such an occasion may arise when the path to be used for the operation is not located near the reference frame or when the markers of the reference frame have to be located at positions that cannot be detected by means of a three-dimensional sensor because of the selected method for the surgical operation.

BRIEF SUMMARY OF THE INVENTION

In view of the above identified circumstances, it is therefore an object of the present invention to provide a reference frame 1) that is structurally stable and can be used during the surgical operation, 2) that can be removably arranged in position when obtaining tomographic images for the purpose of examination and restored to the position prior to the surgical operation and 3) that has markers that can be detected in the tomographic images obtained for the purpose of examination and their positions can be identified on the frame arranged on the body of the patient.

It is another object of the present invention to provide a surgical operation navigator adapted to utilize such a reference frame.

It is another object of the present invention to provide an operative calibration method and an operative calibration apparatus that are flexible enough and adapted to complex paths to be used for surgical operation.

According to a 1st aspect of the present invention, there is provided a reference frame adapted to be fitted to a subject of medical treatment and provided with markers for determining the position or the orientation of the subject, the reference frame comprising:

fixing section for fixing the reference frame with the subject at least three spots along the undulations of the surface thereof; and three or more than three markers detectable at least ether in an X-ray image or in an MRI image of the reference frame, the markers being to be arranged at predetermined positions not connectable by a straight line.

According to a 2nd aspect of the present invention, there is provided a surgical operation navigating system comprising:

a coordinate computing section for computationally determining the coordinates of markers on a reference frame fitted to a subject of medical treatment in a tomographic image of the subject in terms of a coordinate system uniquely defined for the image for examination, the reference frame having three or more than three markers detectable at least either in an X-ray image or in an MRI image thereof, the markers being arranged at predetermined positions not connectable by a straight line; and a correspondence computing section for computationally determining the transformation between the coordinate system for the tomographic image for examination and a coordinate system defined for the real space containing the markers on the basis of the coordinates of the markers as determined by the coordinate computing section in terms of the coordinate system for the tomographic image for examination and the coordinates of the markers as determined in terms of the coordinate system for the real space.

According to a 3rd aspect of the present invention, there is provided a marker to be placed with a predetermined relationship relative to a subject of medical treatment to provide a mark for determining the position or the orientation of the subject, the marker comprising:

a hollow outer shell section formed by using a ceramic material; and a copper sulfate type solution contained in the hollow area of the outer shell.

According to a 4th aspect of the present invention, there is provided a surgical operation navigating system comprising:

a coordinate computing section for computationally determining the coordinates of markers on a reference frame fitted to a subject of medical treatment in a tomographic image of the subject in terms of a coordinate system uniquely defined for the image for examination, the reference frame having three or more than three markers detectable at least either in an X-ray image or in an MRI image thereof, the markers being arranged at predetermined positions not connectable by a straight line;

a first correspondence computing section for computationally determining the transformation between the coordinate system for the tomographic image for examination and a coordinate system defined for the real space containing the markers on the basis of the output of the coordinate computing section and the coordinates of the markers as determined in terms of the coordinate system for the real space;

a second correspondence computing section for computationally determining the transformation between the coordinate system for the real space and a coordinate system uniquely defined for a surgical instrument on the basis of the coordinates of the surgical instrument as determined in terms of the coordinate system for the surgical instrument; and a third correspondence computing section for computationally determining the transformation between the coordinate system for the tomographic image for examination and the coordinate system for the surgical instrument on the basis of the outputs of the first and second correspondence computing sections.

According to a 5th aspect of the present invention, there is provided a surgical operation navigating system comprising:

a coordinate computing section for computationally determining the coordinates of markers on a first reference frame fitted to a subject of medical treatment in a tomographic image of the subject in terms of a coordinate system uniquely defined for the image for examination, the reference frame having three or more than three markers detectable at least either in an X-ray image or in an MRI image thereof, the markers being arranged at predetermined positions not connectable by a straight line;

a correspondence computing section for computationally determining the transformation between the coordinate system for the image for examination and a coordinate system defined for the real space containing the markers on the basis of the output of the coordinate computing section and the coordinates of the markers as determined in terms of the coordinate system for the real space; and a correcting section for correcting the result of the correspondence computing section on the basis of the coordinates of a second reference frame as determined during a surgical operation in terms of the coordinate system for the real space.

According to a 6th aspect of the present invention, there is provided a reference frame comprising:

an anchoring mechanism for rigidly anchoring the reference frame to a subject of medical treatment by utilizing at least three undulated spots on the surface of the body of the subject; and at least three markers arranged on the frame at positions not connectable by a straight line, the markers containing a material adapted to make them detectable at least either in an X-ray image or in an MRI image of the frame.

According to a 7th aspect of the present invention, there is provided a surgical operation navigating system using a reference frame adapted to be rigidly anchored to a subject of medical treatment by utilizing at least three undulated spots on the surface of the body of the subject, the system comprising:

an image acquisition section for acquiring tomographic images of the subject for medical examination with the reference frame fitted to the subject and carrying at least three markers thereon at positions not connectable by a straight line, the markers containing a material adapted to make them detectable at least either in an X-ray image or in an MRI image of the frame;

a marker position detecting section for detecting the positions of the markers in terms of the coordinate system for the tomographic image for examination;

a marker detecting section for detecting the markers on the frame fitted to the subject in the real space; and a registering section for registering the coordinates of the tomographic image for examination and those of the subject by registering the coordinates of the marker positions as detected by the marker position detecting section and the coordinates of the markers as detected by the marker detecting section.

According to an 8th aspect of the present invention, there is provided a reference frame comprising:

fitting section for fitting the reference frame with a subject of medical treatment at least three spots along the undulations of the surface thereof; and markers formed by combining a material easily detectable in an image of first examining method and a material easily detectable in an image of second examining method.

According to a 9th aspect of the present invention, there is provided a calibration method for computing positional/orientational transformation between a subject of medical treatment and a tomographic image of the subject by using the corresponding relationship between the coordinates of a first markers fitted to the subject in the image and the coordinates of the first markers in the real space, the method comprising steps of:

fixing second markers other than the first markers to the subject;

determining the coordinates of the second markers in the image by using the coordinates of the markers in the real space and the corresponding relationship; and computing positional/orientational transformation between the subject and the image of the subject by using the determined coordinates of the second markers.

According to a 10th aspect of the present invention, there is provided a calibration apparatus for computing positional/orientational transformation between a patient to be subjected to a surgical operation a tomographic image of the patient by using the corresponding relationship between the coordinates of a reference frame (first markers) fixed to the patient in the image and the coordinates of the reference frame (markers) in the real space, the apparatus comprising:

a coordinate detecting section for fixing (second) markers other than the reference frame to the patient and determining the coordinates of the markers on the image by using the coordinates of the markers in the real space and the corresponding relationship; and a registering section for computing positional/orientational transformation between the patient and the image of the patient by using the coordinates of the markers determined by the coordinate detecting section.

According to an 11th aspect of the present invention, there is provided a calibration method for computing positional/orientational transformation between a subject of medical treatment and a tomographic image of the subject by using the corresponding relationship between the coordinates of a reference frame (first markers) fitted to the subject in the image and the coordinates of the reference frame in the real space, the method comprising steps of:

fixing (second) markers other than the reference frame (first markers) to the subject and determining the coordinates of the (second) markers on the image by using the coordinates of the (second) markers in the real space and the corresponding relationship; and computing positional/orientational transformation between the subject and the image of the subject by using the markers.

According to a 12th aspect of the present invention, there is provided a method of computing positional/orientational transformation between a subject of medical treatment and a tomographic image of the subject, the method comprising steps of:

fitting a reference frame adapted to be removably placed on the subject and provided thereon with a plurality of first markers;

taking a tomographic image of the subject carrying the reference frame thereon and determining the coordinates of the markers appearing in the image of the subject in terms of a coordinate system defined for the image;

fixing a plurality of second markers to the subject carrying the reference frame and determining the coordinates of the first markers and those of the second markers in terms of a coordinate system defined for the real space;

computing the positional/orientational transformation between the coordinate system defined for the real space and the coordinate system defined for the image on the basis of the coordinates of the first markers in the coordinate system defined for the real space and those of the first markers in the coordinate system defined for the image;

determining the coordinates of the second markers in the coordinate system defined for the image by using the coordinates of the second markers in the coordinate system defined for the real space and the positional/orientational transformation; and computing positional/orientational transformation between the subject and the image of the subject by using the coordinates of the second markers.

According to a 13th aspect of the present invention, there is provided an operative calibration apparatus of computing positional/orientational transformation between a patient to be subjected to a surgical operation and a tomographic image of the patient, the apparatus comprising:

a reference frame to be fitted to the patient, the frame being adapted to be removably placed on the patient and provided thereon with a plurality of first markers;

a first detecting section for taking a tomographic image of the patient carrying the reference frame thereon and determining the coordinates of the markers appearing in the image of the patient in terms of a coordinate system defined for the image;

a second detecting section for fixing a plurality of second markers to the patient carrying the reference frame and determining the coordinates of the first markers and those of the second markers in terms of a coordinate system defined for the real space;

a relationship computing section for computing the positional/orientation transformation between the coordinate system defined for the real space and the coordinate system defined for the image on the basis of the coordinates of the first markers in the coordinate system defined for the real space determined by the first detecting section and those of the first markers in the coordinate system defined for the image;

a coordinate computing section for determining the coordinates of the second markers in the coordinate system defined for the image by using the coordinates of the second markers in the coordinate system defined for the real space determined by the second detecting section and the positional/orientational transformation determined by the relationship computing section; and a registering section for computing positional/orientation transformation between the patient and the image of the patient by using the coordinates of the second markers determined by the coordinate computing section.

According to a 14th aspect of the present invention, there is provided a calibration method of calibrating the position/orientation of a subject of medical treatment and a tomographic image of the subject by using a reference frame securely fitted to the subject, the method comprising steps of:

fixing markers not found on the reference frame to the subject;

defining the positions of the markers in a coordinate system for the image for examination as defined for the image for examination by using the reference frame; and registering the coordinates of the coordinate system for the image for examination and the coordinate system for the real space by detecting the positions of the markers in the coordinate system for the real space as defined for the real space containing the subject.

According to a 15th aspect of the present invention, there is provided a calibration apparatus of calibrating the position/orientation of a patient to be subjected to a surgical operation and a tomographic image of the patient by using a reference frame securely fitted to the subject, the apparatus comprising:

markers not found on the reference frame and adapted to be fitted to the patient;

a position defining section for defining the positions of the markers in a coordinate system for the image for examination as defined for the image for examination by using the reference frame; and an registering section for registering the coordinates of the coordinate system for the image for examination and the coordinate system for the real space by detecting the positions of the markers in the coordinate system for the real space as defined for the real space containing the patient.

According to a 16th aspect of the present invention, there is provided a reference frame adapted to be fitted to a subject of medical treatment and provided with markers for determining the position or the attitude of the subject, the reference frame comprising:

fitting means for fitting the reference frame with the subject at least three spots along the undulations of the surface thereof; and three or more than three markers detectable at least ether in an X-ray image or in an MRI image of the reference frame, the markers being to be arranged at predetermined positions not connectable by a straight line.

According to a 17th aspect of the present invention, there is provided a surgical operation navigating system comprising:

a coordinate computing means for computationally determining the coordinates of markers on a reference frame fitted to a subject of medical treatment in a tomographic image of the subject in terms of a coordinate system uniquely defined for the image for examination, the reference frame having three or more than three markers detectable at least either in an X-ray image or in an MRI image thereof, the markers being arranged at predetermined positions not connectable by a straight line; and a correspondence computing means for computationally determining the transformation between the coordinate system for the image for examination and a coordinate system defined for the real space containing the markers on the basis of the coordinates of the markers as determined by the coordinate computing means in terms of the coordinate system for the tomographic image for examination and the coordinates of the markers as determined in terms of the coordinate system for the real space.

According to an 18th aspect of the present invention, there is provided a surgical operation navigating system comprising:

a coordinate computing means for computationally determining the coordinates of markers on a reference frame fitted to a subject of medical treatment in a tomographic image of the subject in terms of a coordinate system uniquely defined for the image for examination, the reference frame hanging three or more than three markers detectable at least either in an X-ray image or in an MRI image thereof, the markers being arranged at predetermined positions not connectable by a straight line;

a first correspondence computing means for computationally determining the transformation between the coordinate system for the tomographic image for examination and a coordinate system defined for the real space containing the markers on the basis of the output of the coordinate computing means and the coordinates of the markers as determined in terms of the coordinate system for the real space;

a second correspondence computing means for computationally determining the transformation between the coordinate system for the real space and a coordinate system uniquely defined for a surgical instrument on the basis of the coordinates of the surgical instrument as determined in terms of the coordinate system for the surgical instrument; and a third correspondence computing means for computationally determining the transformation between the coordinate system for the image and the coordinate system for the surgical instrument on the basis of the outputs of the first and second correspondence computing means.

According to a 19th aspect of the present invention, there is provided a surgical operation navigating system comprising:

a coordinate computing means for computationally determining the coordinates of markers on a first reference frame fitted to a subject of medical treatment in a tomographic image of the subject in terms of a coordinate system uniquely defined for the tomographic image for examination, the reference frame having three or more than three markers detectable at least either in an X-ray image or in an MRI image thereof, the markers being arranged at predetermined positions not connectable by a straight line;

a correspondence computing means for computationally determining the transformation between the coordinate system for the tomographic image for examination and a coordinate system defined for the real space containing the markers on the basis of the output of the coordinate computing means and the coordinates of the markers as determined in terms of the coordinate system for the real space; and a correcting means for correcting the result of the correspondence computing means on the basis of the coordinates of a second reference frame as determined during a surgical operation in terms of the coordinate system for the real space.

According to a 20th aspect of the present invention, there is provided a reference frame comprising:

an anchoring means for rigidly anchoring the reference frame to a subject of medical treatment by utilizing at least three undulated spots on the surface of the body of the subject; and at least three markers arranged on the frame at positions not connectable by a straight line, the markers containing a material adapted to make them detectable at least either in an X-ray image or in an MRI image of the frame.

According to a 21st aspect of the present invention, there is provided a surgical operation navigating system using a reference frame adapted to be rigidly anchored to a subject of medical treatment by utilizing at least three undulated spots on the surface of the body of the subject, the system comprising:

an image acquisition means for acquiring images of the subject for medical examination with the reference frame fitted to the subject and carrying at least three markers thereon at the positions not connectable by a straight line, the markers containing a material adapted to make them detectable at least either in an X-ray image or in an MRI image of the frame;

a marker position detecting means for detecting the positions of the markers in terms of the coordinate system for the image for examination;

a marker detecting means for detecting the markers on the frame fitted to the subject in the real space; and an registering means for registering the coordinates of the image for examination and those of the subject by registering the coordinates of the marker positions as detected by the marker position detecting means and the coordinates of the markers as detected by the marker detecting means.

According to a 22nd aspect of the present invention, there is provided a reference frame comprising:

fitting means for fitting the reference frame with a subject of medical treatment at least three spots along the undulations of the surface thereof; and markers formed by combining a material easily detectable in an image of a first examining method and a material easily detectable in an image of a second examining method.

According to a 23rd aspect of the present invention, there is provided a calibration apparatus for computing positional/orientational transformation between a patient to be subjected to a surgical operation and a tomographic image of the patient by using the corresponding relationship between the coordinates of first markers on a reference frame fitted to the patient in the image and the coordinates of the reference frame in the real space, the apparatus comprising:

a coordinate detecting means for fitting (second) markers other than the reference frame to the patient and determining the coordinates of the markers on the image by using the coordinates of the markers in the real space and the corresponding relationship; and a registering means for computing positional/orientational transformation between the patient and the image of the patient by using the coordinates of the markers determined by the coordinate detecting means.

According to a 24th aspect of the present invention, there is provided an operative calibration apparatus of computing positional/orientational transformation between a patient to be subjected to a surgical operation and a tomographic image of the patient, the apparatus comprising:

a reference frame to be fitted to the patient, the reference frame being adapted to be removably placed on the patient and provided thereon with a plurality of first markers;

a first detecting means for taking a tomographic image of the patient carrying the reference frame thereon and determining the coordinates of the markers appearing in the image of the patient in terms of a coordinate system defined for the image;

a second detecting means for fitting a plurality of second markers to the patient carrying the reference frame and determining the coordinates of the first markers and those of the second markers in terms of a coordinate system defined for the real space;

a relationship computing means for computing the positional/orientational transformation between the coordinate system defined for the real space and the coordinate system defined for the image on the basis of the coordinates of the first markers in the coordinate system defined for the real space determined by the first detecting means and those of the first markers in the coordinate system defined for the image;

a coordinate computing means for determining the coordinates of the second markers in the coordinate system defined for the image by using the coordinates of the second markers in the coordinate system defined for the real space determined by the second detecting means and the positional/orientational transformation determined by the relationship computing means; and a registering means for computing positional/orientational transformation between the patient and the image of the patient by using the coordinates of the second markers determined by the coordinate computing means.

According to a 25th aspect of the present invention, there is provided a calibration apparatus of calibrating the position/orientation of a patient to be subjected to a surgical operation and a tomographic image of the subject by using a reference frame securely fitted to the subject, the apparatus comprising:

markers not found on the reference frame and adapted to be fitted to the patient;

a position defining means for defining the positions of the markers in a coordinate system for the image for examination as defined for the image for examination by using the reference frame; and a registering section for registering the coordinates of the coordinate system for the image for examination and the coordinate system for the real space by detecting the positions of the markers in the coordinate system for the real space as defined for the real space containing the patient.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

In the drawing.

DETAILED DESCRIPTION OF THE INVENTION

Now, the present invention will be described in greater detail by referring to the accompanying drawing that illustrates preferred embodiments of the invention.

$1^{st}$ Embodiment

Figure 1:
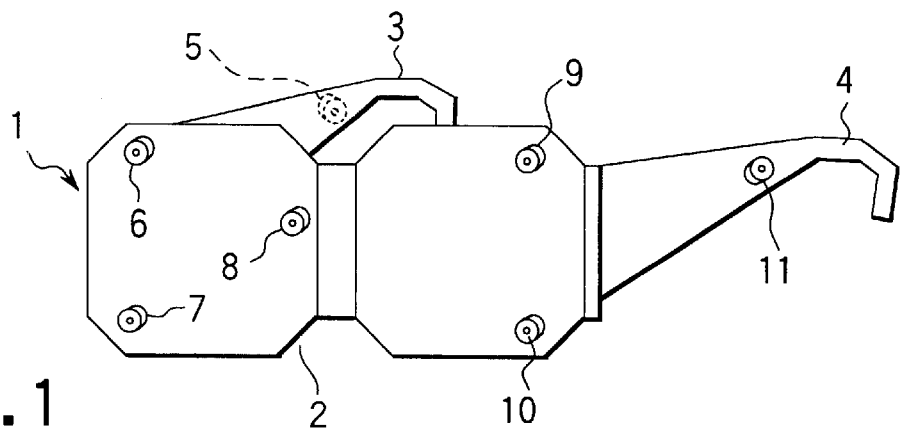
FIG. 1 is a schematic illustration of a first embodiment of a reference frame according to the invention.

FIG. 1 is a schematic illustration of the first embodiment of a reference frame 1 according to the invention. The reference frame 1 has a profile that looks like spectacles or goggles with a frame and comprises a main body 2, a right side member 3 and a left side member 4.

The reference frame 1 is provided with a plurality of markers having a profile that can be clearly identified in an image of the subject of examination such as x-ray and/or MRI. The first embodiment of reference frame is provided with a total of seven markers 5, 6, 7, 8, 9, 10 and 11 that are rigidly fitted to the reference frame 1.

Figure 2:
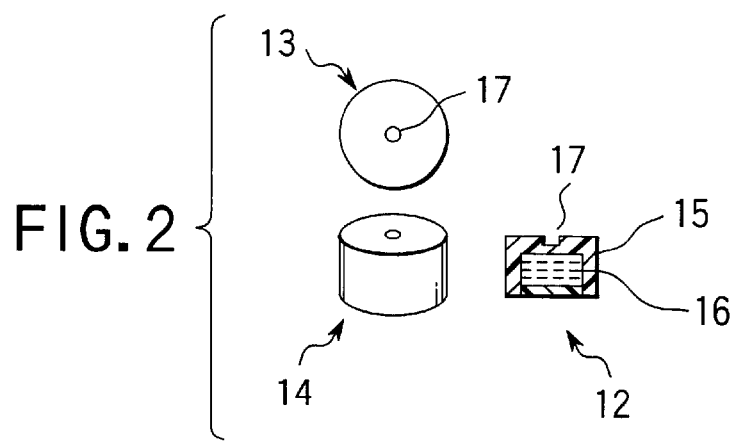
FIG. 2 shows a cylindrical marker adapted to be rigidly fitted to the reference frame of FIG. 1 in cross section and in frontal and lateral elevation.

FIG. 2 shows a cross sectional view 12, a front view 13 and a lateral view 14 of one of the markers adapted to be rigidly fitted to the reference frame 1. The markers 5 through 11 have a cylindrical profile as shown in FIG. 2 and comprise an outer shell section 15 made of a ceramic material that is normally used for artificial bones so that it may be clearly visible in an X-ray image and provided with a probe receiving recess 17 so that the maker may be detected by a sensor probe which will be described hereinafter when the latter is received in it. The outer shell section 15 contains therein a solution 16 that is visible in an MRI image. While the solution may effectively contain copper sulfate or the like to make it visible in the image, it may alternatively contain some other effective chemical.

If only computer tomography (CT) is used for obtaining images for examination, the cylindrical markers may be entirely made of a ceramic material that is normally used for artificial bones. If, on the other hand, only the technique of magnetic resonance imaging (MRI) is used for obtaining images for examination, the outer shell section 15 of the markers may be made of a material other than a ceramic material. For example, it may be made of a plastic material or a acrylic material that does not react with the copper sulfate solution contained in the inside.

Figure 3:
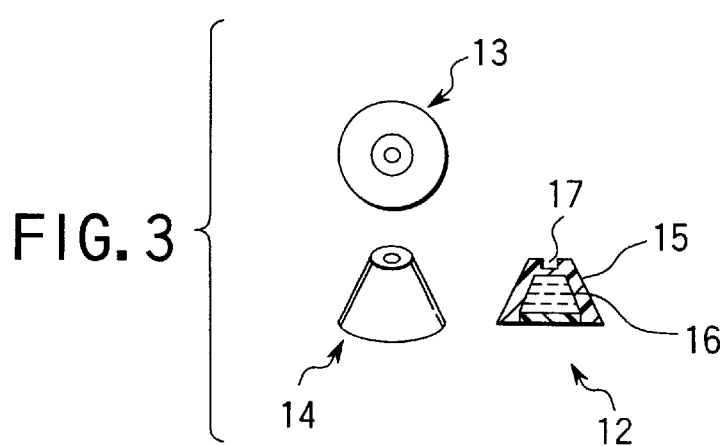
FIG. 3 shows a conical marker also adapted to be rigidly fitted to the reference frame of FIG. 1 in cross section and in frontal and lateral elevation.

FIG. 3 shows a conical marker also adapted to be rigidly fitted to the reference frame of FIG. 1 in cross section and in frontal and lateral elevation. A marker having a conical profile provides an advantage that its attitude can easily be recognized and it can be reliably fitted to the reference frame main body.

Once the reference frame 1 is fitted to the head of the subject of examination, it can be rigidly secured to the head at the tops of the left and right ears and at the nasal projection. The reference frame 1 can be removed from the subject of examination when it is not used for taking tomographic images for medical examination or for a surgical operation.

Figure 4:
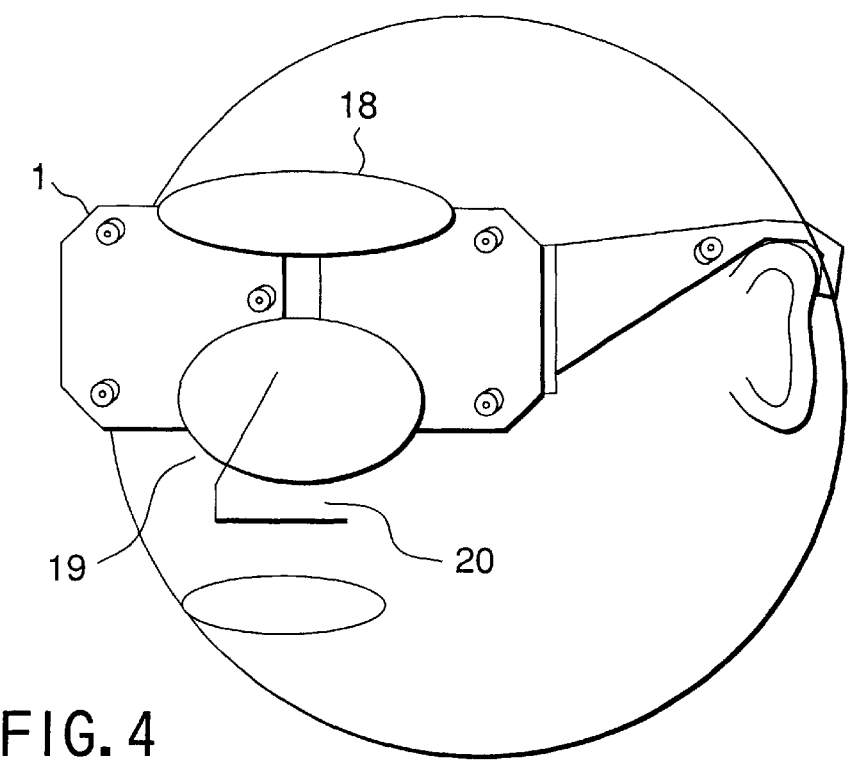
FIG. 4 is a schematic illustration of a reference frame according to the invention and made of a material that hardens with time.

If the reference frame 1 is not very stable on the subject of examination, a filling material that hardens with time (e.g., silicone rubber) may be filled into the gap separating the reference frame 1 and the opposite surface of the subject of examination and also laid on the reference frame 1 as shown in FIG. 4 in order to make the frame 1 secure on the subject of examination. In FIG. 4, a filling material is put on the forehead of the subject of examination (as indicated by reference numeral 18) and on the nose of the subject of examination (as indicated by reference numeral 19).

Of the seven markers 5 through 11, the marker 8 located near the center of the face is not located on the axis of symmetry of the frame 1. This is because the viewer of the tomographic image of the head of the subject of examination can tell the top and the bottom thereof by seeing the marker 8 that is displaced from the axis of symmetry. More specifically, the viewer of the tomographic image can easily recognize if it shows the right side coordinate system or the left side coordinate system.

Now, a surgical operation navigating system utilizing the above embodiment of reference frame will be described below.

Figure 5:
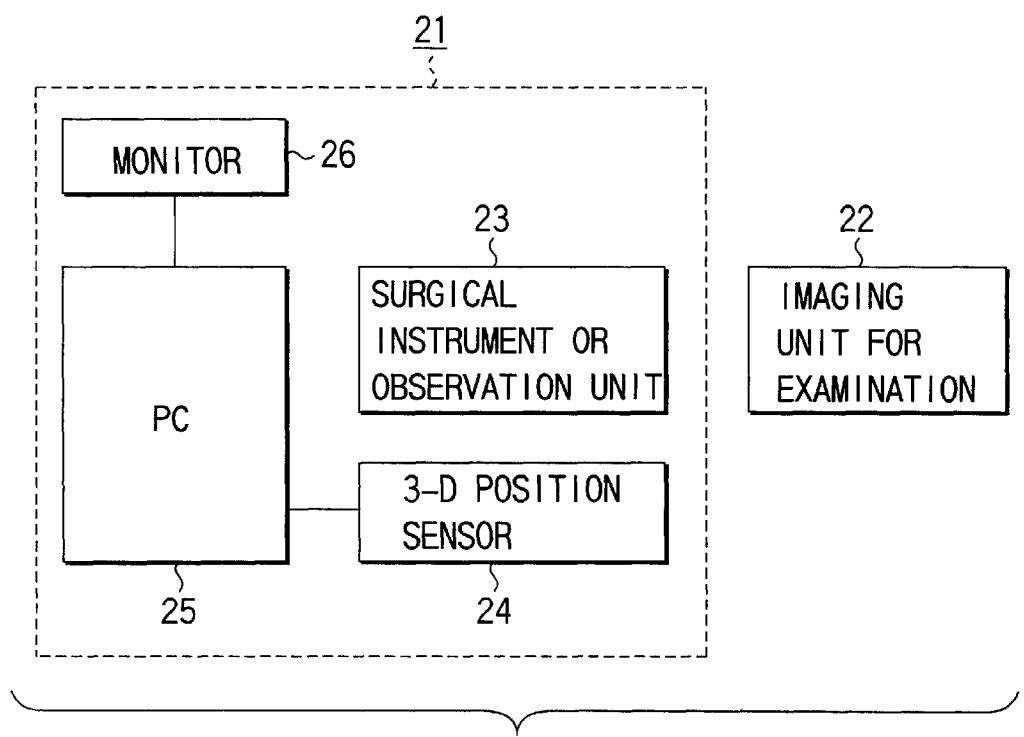
FIG. 5 is a schematic block diagram of a first embodiment of surgical operation navigating system according to the invention.

FIG. 5 is a schematic block diagram of a first embodiment of surgical operation navigating system according to the invention. The surgical operation navigating system 21 is typically used with an imaging unit 22 for examination that is adapted to acquire an X-ray (CT) image or an MRI image and convert it into digital image data that can be processed by a computer.

The surgical operation navigating system 21 comprises a surgical instrument or observation unit 23 for observing the site of operation, a 3-D position sensor 24 for detecting the attitude of the surgical instrument or observation unit 23, a personal computer (PC) 25 for processing the digital data it receives from the imaging unit 22 and generating various pieces of navigation-related information on the basis of the data it receives from the 3-D position sensor 24 and a monitor 26 for displaying navigation-related information and image information coming from the PC 25.

Before describing further the surgical operation navigating system 21 having the above described configuration, some of the terms used herein will be summarily described below.

Coordinate System

For the purpose of the present invention, a number of coordinate systems that are necessary for navigation will be defined. The surgical instrument (which may be the observation unit) to be used for a surgical operation may include an endoscope, a surgical microscope, forceps and other surgical instruments, each of which may have its own coordinate system for defining the three-dimensional position/orientation of it. A coordinate system E is used to define the three-dimensional position/orientation of a surgical instrument. In other words, the position of the surgical instrument in an xyz-coordinate system is expressed by $E(x_E, y_E, z_E)$.

The images of the subject acquired for examination may be those of MRI, CT or SPECT (single photon emission computed tomography). The three-dimensional structure of the subject of the images can be reconstructed by combining the two-dimensional tomographic images. Then, a coordinate system P can be defined for the reconstructed three-dimensional structure. Assume that a coordinate system P is used to define the three-dimensional position/orientation of the structure. In other words, the position of the structure in an xyz-coordinate system is expressed by $P(x_P, y_P, z_P)$.

Assume that MRI images used. MRI images are normally picked up along the central axis of the body of the subject of examination. If the axis is defined as Z-axis, a tomographic image is normally acquired on an xy-plane. Assume also that tomographic images are acquired along the Z-axis at a pitch of dz (mm/image). If the horizontal direction of the tomographic image runs along the x-axis and the resolution of the image pixels in the x-direction is dx (mm/pixel), whereas the vertical direction of the tomographic image runs along the y-axis and the resolution of the image pixels in the y-direction is dy (mm/pixel), the origin of the operation of picking up the image can be defined in terms of the x-, y- and z-axes and a three-dimensional position in the image can be defined in terms of (idx, jdy, kdz), by using indexes (i, j, k) for the x-, y- and z-directions of the image. The coordinate system of the image as defined above is referred to as coordinate system $P(x_P, y_P, z_P)$ of the image for examination.

A coordinate system can be defined for the real space where the subject of examination exists. Such a real space coordinate system w may be regarded as reference coordinate system that is defined in the operating room in terms of $W(x_W, y_W, z_W)$.

Coordinate Registration

Coordinates of a plurality of coordinate systems can be registered to define the positional relationship of the coordinate systems. In other words, coordinate values of coordinate system A can be transformed into corresponding ones of coordinate system B (or vice versa) by registering them. More specifically, the operation of coordinate registration may be referred to as an operation of determining coordinate transformation parameters for transforming coordinate system A into coordinate system B. In mathematical terms, if a homogeneous transformation matrix is used for determining coordinate transformation parameters and coordinate values $(x_A, y_A, z_A)$ in coordinate system A correspond to coordinate values $(x_B, y_B, z_B)$ in coordinate system B, the matrix can take the form of a 4×4 matrix expressed by $_BH_A$ as shown below.

$$\begin{bmatrix} {}^xB \\ {}^yB \\ {}^zB \\ 1 \end{bmatrix} = {}^BH_A \begin{bmatrix} {}^xA \\ {}^yA \\ {}^zA \\ 1 \end{bmatrix}$$

A technique other than the one using a homogeneous transformation matrix may be used for expressing the above. For example, a technique of using rotation matrix R and a translation vector t as expressed by formula below or a technique of using quaternions for rotation matrix R may alternatively be used.

$$\begin{bmatrix} {}^xB \\ {}^yB \\ {}^zB \end{bmatrix} = R \begin{bmatrix} {}^xA \\ {}^yA \\ {}^zA \end{bmatrix} + t$$

Any of the above techniques may be used for determining coordinate transformation parameters.

Operative Navigation

Figure 6:
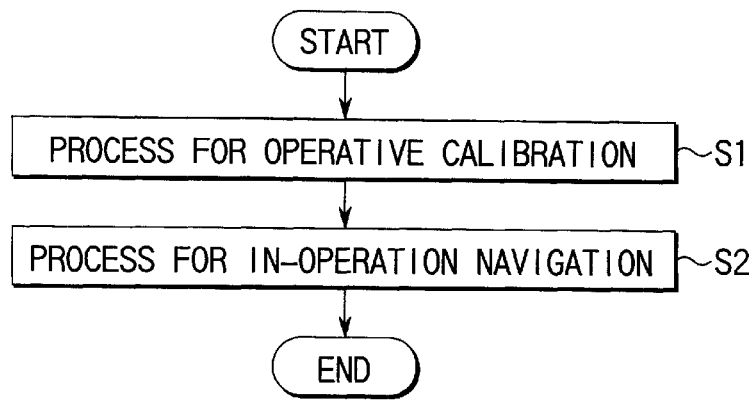
FIG. 6 is a flow chart of a process of navigating a surgical operation according to the invention.

The term "operative navigation" as used herein refers to a process including both operative calibration and in-operation navigation. As shown in FIG. 6, for a process of operative navigation, the PC 25 firstly executes a process for operative calibration (Step S1) and then a process for in-operation navigation (Step S2).

Operative Calibration

This refers to a process of registering the coordinate system of the image obtained for examination and the real space coordinate system where the subject exists.

In-operation Navigation

This refers to a process of registering the coordinate system of surgical instrument E and the coordinate system of a real space W for defining the position/orientation of the subject as a function of the motion of the instrument and indicating:

1) the positional relationship between the target point (or the target itself) of the surgical operation and the surgical instrument; or
2) the position/orientation of the surgical instrument relative to the coordinate system of the real space and the coordinate registered coordinate system of the image obtained for examination.

Figure 7:
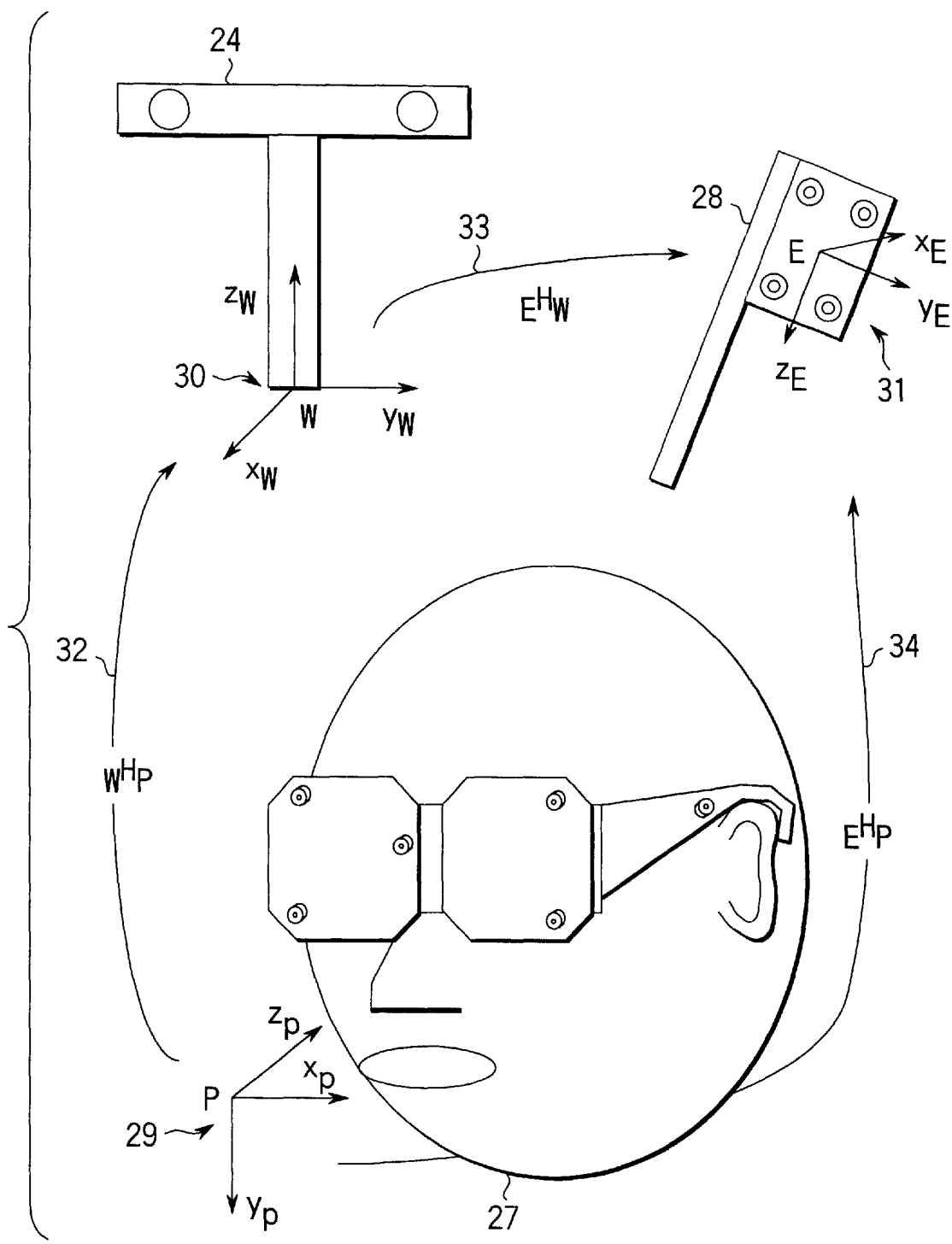
FIG. 7 is a schematic illustration of a possible relationship of different coordinate systems to be established when navigating a surgical operation.

FIG. 7 is a schematic illustration of a possible relationship of different coordinate systems to be established when navigating a surgical operation. Referring to FIG. 7, there are shown a subject 27 of surgical operation, surgical instrument 28 to be used for the surgical operation and a 3-D position sensor 24 for detecting the three-dimensional position/attitude of the subject 27 and that of the surgical instrument 28. Therefore, there may be defined a coordinate system 29 for the image for examination as acquired by the imaging unit 22 to contain the target portion of the subject 27, a coordinate system 30 for a real space defined in the operating room and containing the 3-D position sensor 24 and the subject 27 and a coordinate system 31 for the surgical instrument 28. In order to register the coordinate systems, it is necessary to determine the coordinate transformation parameters to be used for the coordinate systems. Then, there may be coordinate transformation parameters $_EH_P$ for defining the coordinate transformation 32 from the coordinate system 29 for the image for examination to the coordinate system 30 for the real space, coordinate transformation parameters $_EH_W$ for defining the coordinate transformation 33 from the coordinate system 30 for the real space to the coordinate system 31 for the surgical instrument and coordinate transformation parameters $_EH_P$ for defining the coordinate transformation 34 from the coordinate system 29 for the image for examination to the coordinate system 31 for the surgical instrument.

Figure 8:
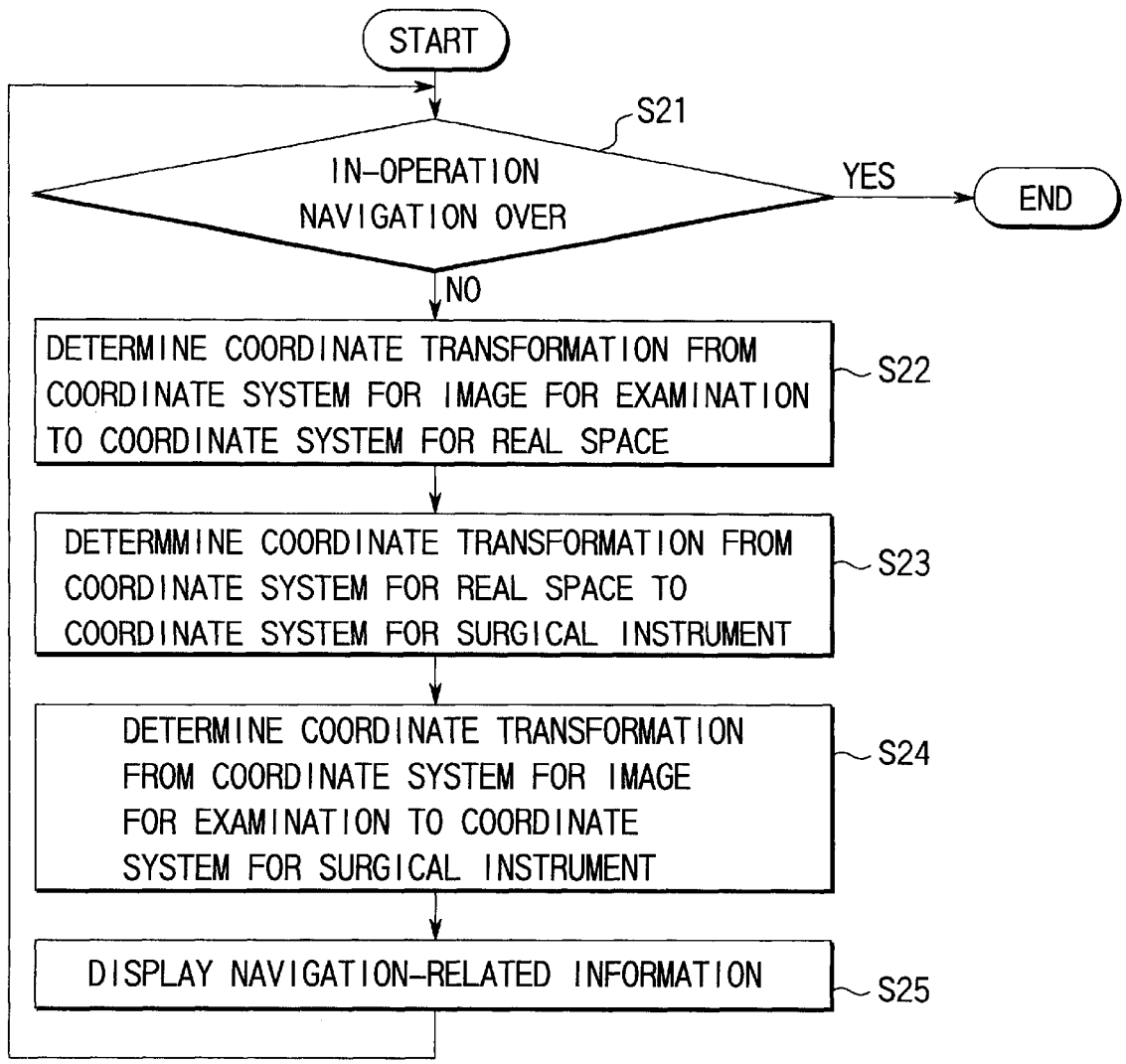
FIG. 8 is a flow chart of the in-operation navigation processing step of FIG. 6, illustrating the basic steps contained therein.

FIG. 8 is a flow chart of the in-operation navigation processing step, or Step S2 of FIG. 6, to be executed by the PC 25, illustrating the basic steps contained therein.

Referring to FIG. 8, firstly it is checked if the in-operation navigation processing is to be terminated or not (Step S21) and, if it is found that the in-operation navigation processing is not to be terminated, the coordinate transformation parameters $_WH_P$ for defining the coordinate transformation from the coordinate system 29 for the image for examination to the coordinate system 30 for the real space are computationally determined (Step S22) by utilizing the result of the in-operation navigation processing in the above Step S1.

Subsequently, the coordinate transformation parameters $_EH_W$ for defining the coordinate transformation from the coordinate system 30 for the real space to the coordinate system 31 for the surgical instrument are computationally determined (Step S23) by detecting the 3-D position/attitude of the surgical instrument 28 by the 3-D position sensor arranged within the real space.

Then, the coordinate transformation parameters $_EH_P$ for defining the coordinate transformation from the coordinate system 29 for the image for examination to the coordinate system 31 for the surgical instrument are computationally determined (Step S24) by utilizing the result of the above Step S22 and that of the Step S23. More specifically, they can be determined by way of a multiplication of matrixes of 4 rows and 4 columns as shown below.

$$_EH_P = {}_EH_W \, {}_WH_P$$

Finally, (1) the position of the surgical instrument 28 in the coordinate system 29 for the image for examination and (2) the position of the target as transferred from the coordinate system 29 for the image for examination to the coordinate system 31 for the surgical instrument are computationally determined by using the coordinate transformation parameters $_EH_P$ for the coordinate transformation from the coordinate system 29 for the image for examination to the coordinate system 31 for the surgical instrument determined in the Step 24 to obtain navigation-related information required for the surgical operation, which information is then displayed on the display screen of the monitor 26 (Step S25).

Note that the method of displaying the obtained navigation-related information on the display screen of the monitor 26 is not described here because it is not essential to the present invention. In the following, the process of in-operation navigation including the operation of coordinate registration will be discussed. For example, either of the two techniques as described below may be employed for displaying the information when an endoscope is used as surgical instrument 28.

(1) $1^{st}$ Technique: In-operation Navigation Using Three-orthogonal Views

Figure 9:
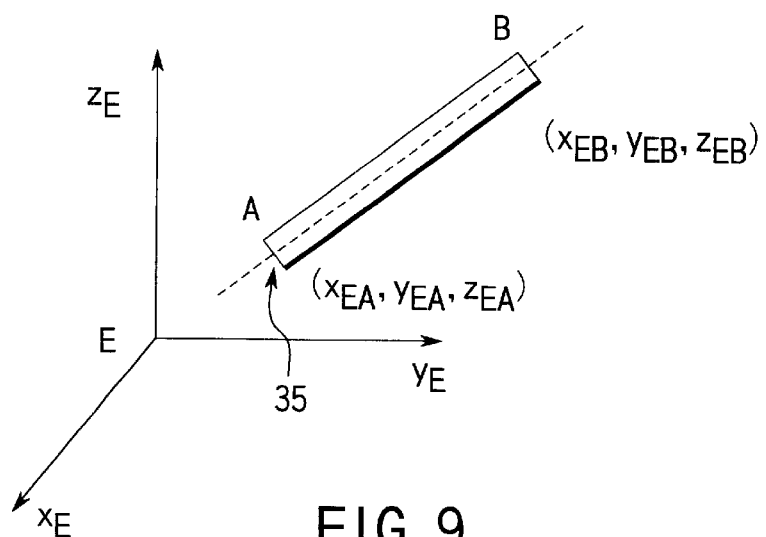
FIG. 9 is a schematic illustration of a coordinate system that can be used for defining an endoscope.

With this technique, endoscope coordinate system $E(x_E, y_E, z_E)$ is defined to navigate the endoscope to the target. The target is defined within the image for examination. Therefore assume here that the point of target P0 is defined by ($x_{P0}$, $y_{P0}$, $z_{P0}$) in the coordinate system 29 for the image for examination. Referring to FIG. 9, assume that the endoscope is described by a line segment model AB having the front end 35 at $A(x_{EA}, y_{EA}, z_{EA})$ and the other end at $B(x_{EB}, y_{EB}, z_{EB})$ in the coordinate system for the surgical instrument, which is the endoscope. The front end A and the other end B of the endoscope can be defined in terms of the coordinate system 29 for the image for examination as $(x_{PA}, y_{PA}, z_{PA})$ and $(x_{PB}, y_{PB}, z_{PB})$ respectively by using the coordinate transformation parameters for the coordinate transformation from the coordinate system 31 for the surgical instrument to the coordinate system 29 for the image for examination, or $_PH_E = (_EH_P)^{-1}$, and the formula below.

$$\begin{bmatrix} ^xPA \\ ^yPA \\ ^zPA \\ 1 \end{bmatrix} = P^H E \begin{bmatrix} ^xEA \\ ^yEA \\ ^zEA \\ 1 \end{bmatrix}, \begin{bmatrix} ^xPB \\ ^yPB \\ ^zPB \\ 1 \end{bmatrix} = P^H E \begin{bmatrix} ^xEB \\ ^yEB \\ ^zEB \\ 1 \end{bmatrix}$$

Figure 10:
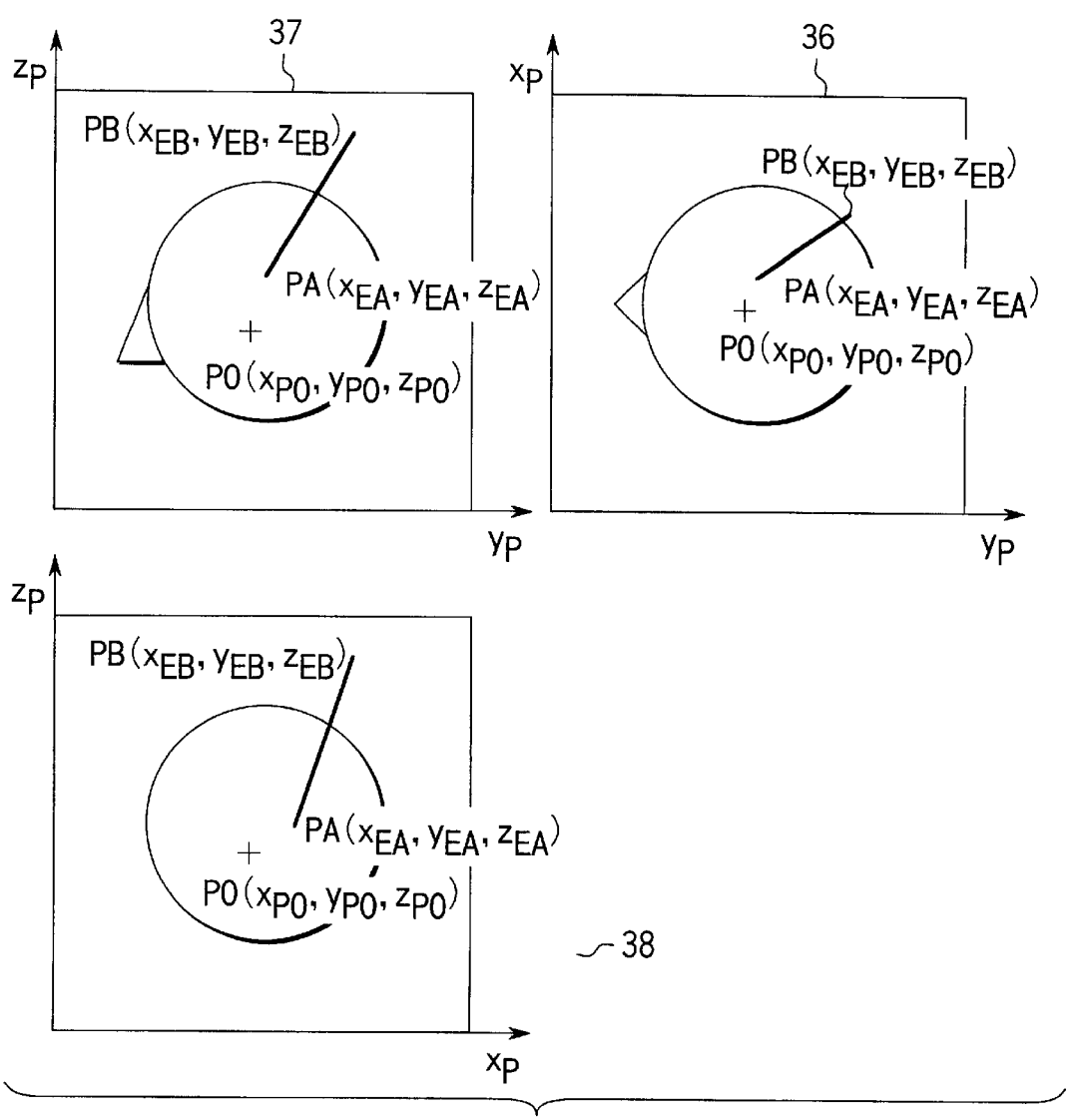
FIG. 10 is a schematic illustration of an orthogonal view image that can be used for examination.

Thus, if an orthogonal view having xy plane 36, yz plane 37 and zx plane 38 are used for the image for examination as shown in FIG. 10, the target point P0 $(x_{P0}, y_{P0}, z_{P0})$ and the endoscope ends $(x_{PA}, y_{PA}, z_{PA})$ and $(x_{PB}, y_{PB}, z_{PB})$ can be displayed on the orthogonal view. Therefore, by looking at the orthogonal views, the doctor can visually realize the positional relationship the target has among the three coordinate systems.

Figure 11:
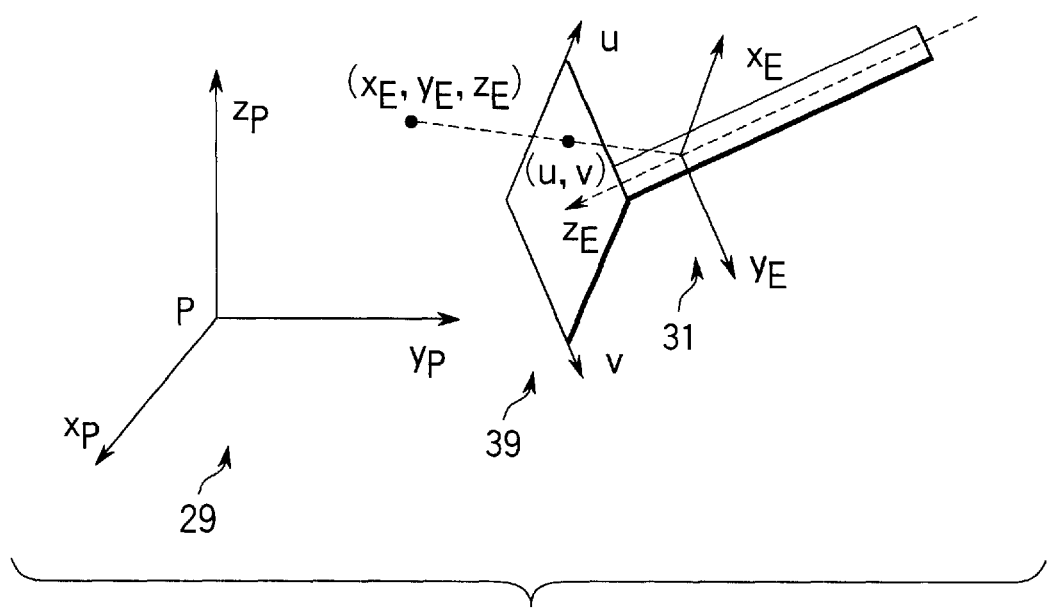
FIG. 11 is a schematic illustration of a coordinate system that can be used for an endoscope.

(2) $2^{nd}$ Technique: In-operation Navigation Using Visual Field Coordinate Transformation With this technique, coordinate system 31 for the surgical instrument is defined to navigate the endoscope to the target as shown in FIG. 11. The target is defined in terms of the coordinate system 29 for the image for examination. Therefore assume here that the point of target is defined by $(x_P, y_P, z_P)$ in the coordinate system 29 for the image for examination. On the other hand, if a point in a two-dimensional image is defined by (u, v) to establish the correspondence of the coordinate system for the two-dimensional image (visual field coordinate system 39) that is defined for the visual field of the endoscope to the endoscope coordinate system (coordinate system 31 for the surgical instrument), it is expressed by a non-linear function as shown below.

$$\begin{bmatrix} u \\ v \end{bmatrix} = f(^xE, ^yE, ^zE)$$

The operation of defining such a non-linear function is referred to that of camera calibration of an endoscope system and described in detail in R. Tsai, "A versatile camera calibration technique for high-accuracy 3-D machine vision metrology using off-the-shell TV cameras and lenses", IEEE Journal of Robotics and Automation, Vol. 3, No. 4, pp. 323–344, August 1987. Therefore, the operation would not be described here any further.

When the endoscope moves with time in the real space, the location of the target in the subject can be determined in terms of to the visual field coordinate system 39 of the endoscope by detecting the endoscope in the coordinate system 30 for the real space by the 3-D position sensor 24. The detection of the endoscope by using the 3-D position sensor is equivalent to the operation of computationally determining the coordinate transformation parameters for defining the coordinate transformation from the coordinate system 30 for the real space to the endoscope coordinate system E (coordinate system 31 for the surgical instrument).

In other words, the coordinate transformation parameters $_EH_W$ as defined below can be obtained by the detection.

$$\begin{bmatrix} ^xE \\ ^yE \\ ^zE \\ 1 \end{bmatrix} = E^H W \begin{bmatrix} ^xW \\ ^yW \\ ^zW \\ 1 \end{bmatrix}$$

Thus, the target defined in terms of the coordinate system 29 for the image for examination can now be defined in terms of the endoscope coordinate system (coordinate system 31 for the surgical instrument) by using the equation below that utilizes the above equation.

$$\begin{bmatrix} ^xE \\ ^yE \\ ^zE \\ 1 \end{bmatrix} = E^H W \begin{bmatrix} ^xW \\ ^yW \\ ^zW \\ 1 \end{bmatrix} = E^H W W^H P \begin{bmatrix} ^xP \\ ^yP \\ ^zP \\ 1 \end{bmatrix}$$

Then, by using this formulas and the formulas below, the target that is already defined in terms of the coordinate system 29 for the image for examination now can be defined in terms of the coordinate system 39 for the visual field of the endoscope.

$$\begin{bmatrix} u \\ v \end{bmatrix} = f(^xE, ^yE, ^zE)$$

Thus, if the position/attitude of the endoscope changes in the real space, the target can be displayed in the visual field of the endoscope so as to navigate the endoscope.

Therefore, it is possible to display a more complex operation of navigating the surgical instrument to the target on the basis of the above described basic operation. For instance, if the target is defined as a wire frame image in the coordinate system 29 for the image for examination, then the opposite ends of each of the line segments of the wire frame image can be defined in terms of the coordinate system 39 for the visual field of the endoscope in a manner as described above. Thus, the wire frame model can be displayed in the coordinate system 39 for the visual field of the endoscope by drawing lines connecting the respective opposite ends in the two-dimensional visual field.

Figure 12:
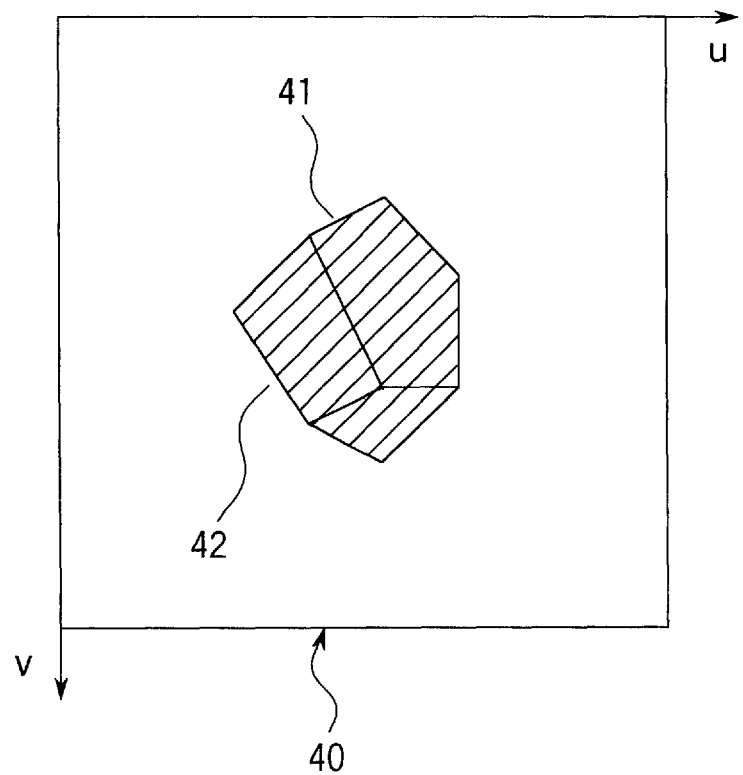
FIG. 12 is a schematic illustration of a wire frame model shown in a coordinate system provided for the view angle of an endoscope.

FIG. 12 schematically illustrates such an operation. Referring to FIG. 12, the position, the size and the profile of the target 41 can be visually displayed to the doctor by laying the wire frame model 42 of the target on the target 41 itself in the visual field coordinate system 40 so that the doctor can "feel" the target 41.

Additionally, the target can be indicated by a vector extending from the center of the visual field of the endoscope so that the doctor can see where the target is and how far it is from the endoscope if it is out of the visual field of the endoscope.

So much for in-operation navigation, now, the operative calibration of Step S1 in FIG. 6 that precedes the in-operation navigation of Step S2 will be discussed further below.

Figure 13:
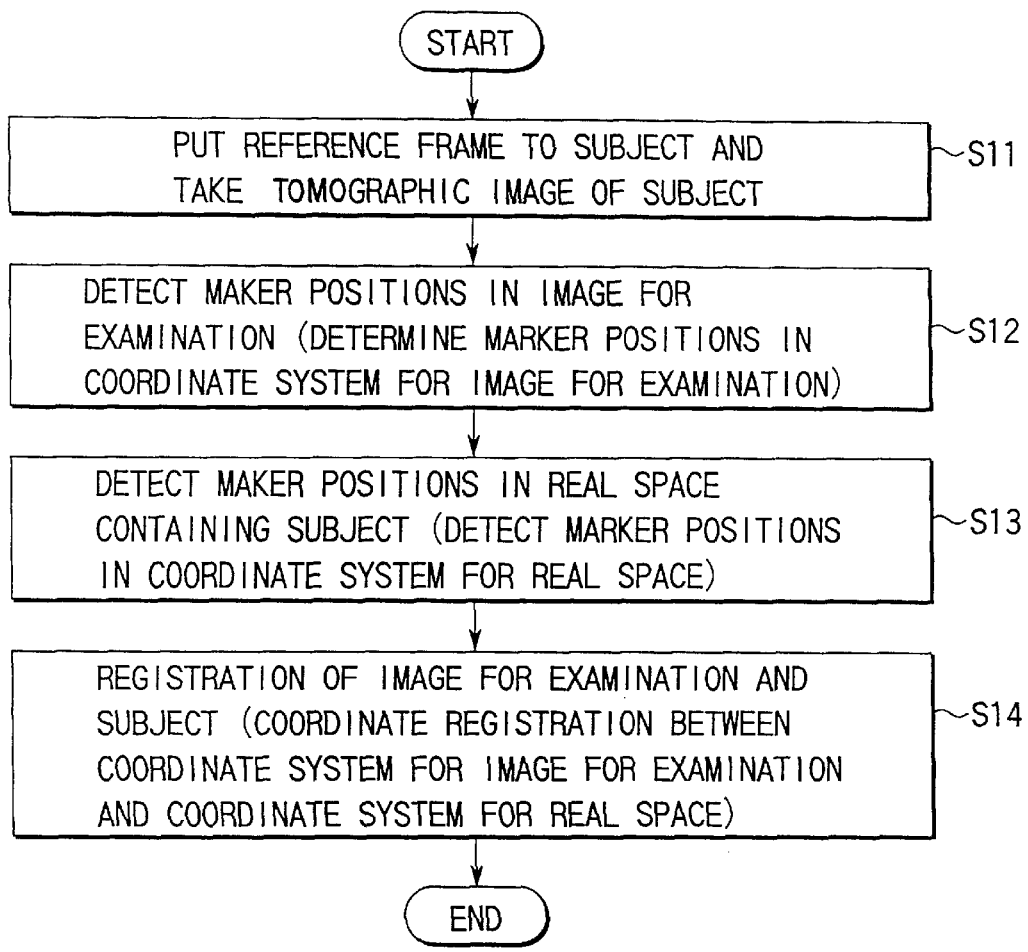
FIG. 13 is a flow chart of the operative calibration processing step of FIG. 6, illustrating the basic steps thereof.
Figure 14:
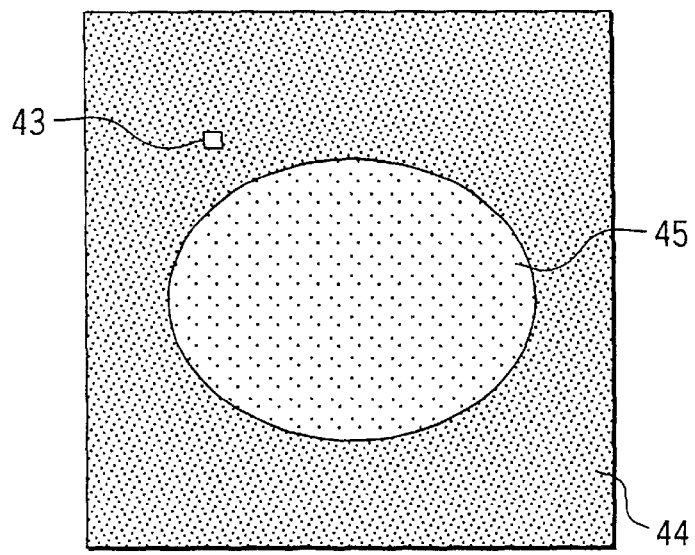
FIG. 14 is a schematic illustration of an MRI tomographic image obtained by using a cylindrical marker as shown in FIG. 2.

FIG. 13 is a flow chart of the operative calibration of Step S2 of FIG. 6, illustrating the basic steps thereof.

Firstly, the reference frame 1 is put onto the subject 27 and an image is acquired for examination by the imaging unit 22 (Step S11). Then, the markers are detected in the coordinate system for the image for examination (Step S12). Note that the positions of the markers are defined three-dimensionally in terms of the coordinate system 29 for the image for examination. Assume that they are located at $(x_P(i), y_P(i), z_P(i))$ (i=1, 2, . . . , n). Note that n=7 in the case of the reference frame 1 illustrated in FIG. 1.

Thereafter, the markers are detected in the real space where the subject 27 is found (Step S13). Thus, the target found in the image for examination can be aligned with itself in the real space by locating the markers detected in Step S12 in the coordinate system 30 for the real space where the subject 27 is found by the 3-D position sensor 24 and registering the coordinates of both the coordinate system 30 for the real space where the subject 27 is found and the coordinate system 29 for the image for examination. Assume that the three-dimensional positions of the detected markers are expressed by $(x_W(i), y_W(i), z_W(i))$ (i=1, 2, . . . , n).

Then, the coordinates of the coordinate system 29 for the image for examination and the coordinate system 30 for the real space where the subject 27 is found are registered by using $(x_P(i), y_P(i), z_P(i))$ (i=1, 2, . . . , n) of the markers in the coordinate system 29 for the image for examination as detected in Step S12 and $(x_W(i), y_W(i), z_W(i))$ (i=1, 2, . . . , n) of the markers in the coordinate system 30 for the real space where the subject 27 is found as detected in Step S13 (Step S14). Thus, the coordinate transformation 32 from the coordinate system 29 for the image for examination to the coordinate system 30 for the real space is defined.

Now, the above steps will be discussed further. While the image for examination is an MRI image in the following description, it may be replaced by a CT image or some other image without any problem.

Firstly, Step S11 will be discussed below.

In Step S11, the reference frame 1 is put onto the subject 27. If the reference frame 1 is not rigidly secured to the subject 27, a filling material 18, 19 that hardens with time may be filled into the gaps separating the reference frame 1 and the nasal projection and the forehead of the subject 27 as shown in FIG. 4 in order to make the frame 1 secure on the subject of examination. Thereafter, tomographic images of the subject 27 are taken for medical examination and image data are obtained therefrom for the purpose of medical examination.

Now, Step S12 will be discussed below.

In Step S12, the marker regions are extracted from the image data and their positions are determined in terms of the coordinate system 29 for the image for examination. Thus, the image data are obtained from the tomographic images and the regions occupied by the markers 5 through 11 are extracted from the images.

Assume here that cylindrical markers as shown in FIG. 2 are used. Since the cylindrical markers contain a solution 16 that becomes clearly visible in an MRI image, the marker regions 43 can be clearly discriminated from the head 45 of the subject 27 in the MRI image 44. Additionally, since the markers are arranged on the reference frame 1, they are separated from the head 45 of the subject 27. When these findings are taken into consideration, it is now possible to define the marker regions as regions whose density is found within a certain range. More specifically, if the density g (i, j) of a pixel (i, j) of the MRI image satisfies the requirement expressed by the formula below, it is registered as candidate of a marker region. Note that $g_{min}$ and $g_{max}$ in the formula are constants.

$$g_{min} \leq g(i, j) \leq g_{max}$$

After processing each of the obtained tomographic images in a manner as described above, the data for the candidates of marker regions are combined as three-dimensional volume data.

Then, the marker regions registered as volume data are three-dimensionally labeled. Thereafter, geometrically characteristic values are determined for each of the labeled volume regions to judge if the volume region really corresponds to a marker region. Parameters that can be used for the judgment may include:

1) the three-dimensional volume of the volume region; and
2) the length of the radius and that of the medial axis (axis of rotation) when the volume region is approximated as cylinder.

If these values are found within respective certain ranges, the region is judged to be as marker volume region.

Figure 15:
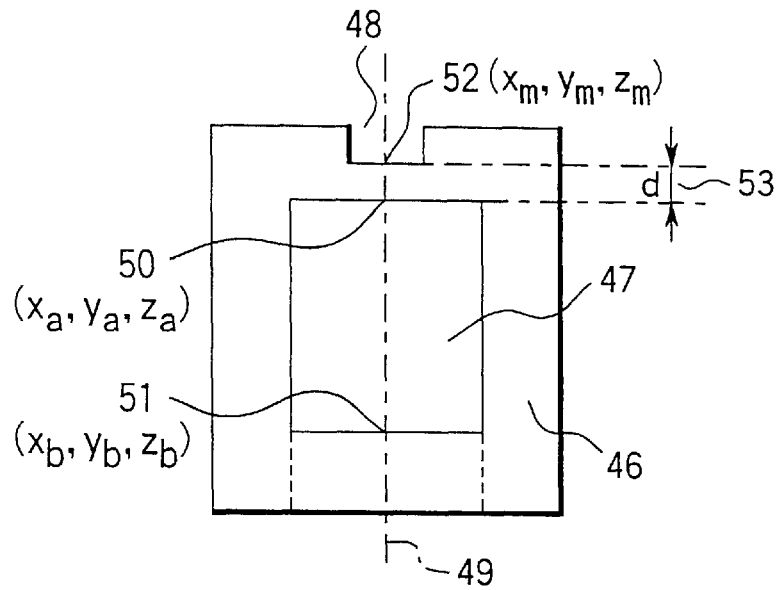
FIG. 15 is a schematic illustration of a graphic model of a marker volume region.

FIG. 15 is a schematic illustration of a graphic model of a registered marker volume region. For forming the model, the marker having a marker shell section 46, a solution 47 contained in the shell and a probe receiving recess 48 is defined in terms of the medial axis 49 of the solution 47 contained in the outer shell section 46 and the opposite ends A 50 and B 51 of the medial axis 49 of the solution 47 contained in the outer shell. Assume that the coordinate values of the opposite ends A 50 and B 51 in terms of the coordinate system 29 for the image for examination are respectively $(x_a, y_a, z_a)$ and $(x_b, y_b, z_b)$. On the other hand, the marker position 52 defined by the coordinate system 29 for the image for examination is point where the main axis 49 and cuter marker shell 46 are changed externally in the probe receiving recess 48 in FIG. 15. Its coordinate value are defined as $(x_m, y_m, z_m)$ by the coordinate system 29 for the image for examination and the distance between the end A 50 and the reference position 52 of the marker is distance d 53.

Then, the reference position 52 of the maker is obtained by the formula below on the basis of the end A 50 and the end B 51 as determined by the above technique.

$$\begin{bmatrix} x_m \\ y_m \\ z_m \end{bmatrix} = \frac{d}{\sqrt{(x_b - x_a)^2 + (y_b - y_a)^2 + (z_b - z_a)^2}} \begin{bmatrix} x_b - x_a \\ y_b - y_a \\ z_b - z_a \end{bmatrix} + \begin{bmatrix} x_a \\ y_a \\ z_a \end{bmatrix}$$

While an image processing technique is used for detecting the markers in Step S12 in the above description, the operator of the system may manually detect the markers, viewing the image for examination.

Anyhow, the markers fixed to the reference frame 1 are detected in terms of the coordinate system 29 for the image for examination. Note that, as described above, the number of markers is n and their positions are defined by $(x_P(i), y_P(i), z_P(i))$ (i=1, 2, . . . , n).

In the case of CT images, on the other hand, the following processing operation will be conducted.

The outer shell sections 46 of the markers are made visible in CT images for examination. Therefore, the regions of the outer shell sections 46 of the markers are extracted from the image and subsequently, as in the case of the MRI image, they are three-dimensionally restructured. The outer shell sections 46 contains a void in the inside that is extracted from the MRI image but not from the CT image. Therefore, the void has to be filled to make the markers appear quasi-cylindrical. The approximated cylinders are then subjected to the processing operation described above for the MRI image to locate the markers at the probe receiving recesses 48 thereof.

If the markers have a conical or truncated cone profile or a conical recess as shown in FIG. 3, the positions of the markers can be detected from the image by locating them at the top of the marker or the bottom of the recess thereof, whichever appropriate, as in the case of markers having a cylindrical profile.

Now, Step S13 will be discussed in detail below.

Figure 16:
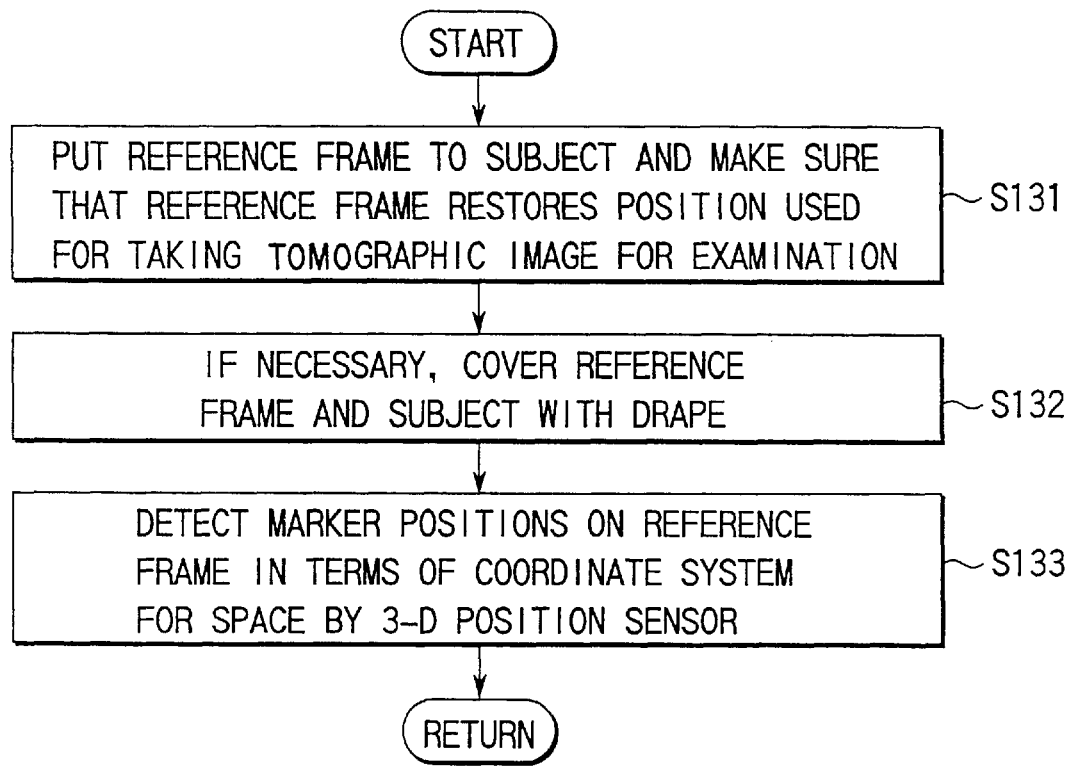
FIG. 16 is a flow chart of the step of detecting a marker in a real space containing a subject of examination in FIG. 13.

This Step S13 corresponds to the calibration process (coordinate registration process) conducted immediately before the surgical operation to be carried out on the subject 27. Step S13 proceeds in a manner as illustrated in FIG. 16.

Firstly, the reference frame 1 that is used for obtaining an image for examination is fitted to the subject 27 once again and it is made sure that the frame 1 is put to the subject 27 exactly same as before (Step S131). The filling material 18, 19 that hardens with time may effectively be used for correctly positioning the frame 1.

If the surgical operation has to be conducted in a very clean environment, an iodine containing drape may be put on the reference frame 1 (Step S132). When a drape is used, care should be taken to make at least three of "the front ends (probe receiving recesses 48) of the markers 5 through 11 arranged on the reference frame 1" are unhidden by the drape. As a result, both the surface of the body of the subject 27 that is not specifically cleaned and the reference frame 1 can be controlled in a clean environment.

Then, the position of the subject 27 is registered in the real space by the 3-D position sensor 24 that can be operated in a clean environment (Step S133). The 3-D position sensor 24 may be a sensor equipped with a probe, or sensor probe. Such a sensor is adapted to detect "the front end (probe receiving recess 48) of each of the markers arranged on the reference frame 1" that are not hidden by the drape to locate the markers in terms of the coordinate system 30 for the real space.

Sensor probes that can be used for this purpose include optical sensor systems adapted to detect infrared rays and mechanical sensor systems having a mechanical arm.

An optical sensor system adapted to detect infrared rays comprises a sensor probe that is typically provided with a plurality of IR emitting diodes (LEDs) and the infrared rays emitted from the diodes are detected by a multiple view CCD camera (stereoscopic camera (arranged in the coordinate system 30 for the real space)) to locate the IR emitting diodes in the coordinate system 30 for the real space on the basis of the theorem of triangulation. As the IR emitting diodes are located in the coordinate system 30 for the real space on a one by one basis, the front end of the probe can also be located in the coordinate system 30 for the real space.

On the other hand, a mechanical sensor system having a mechanical arm is adapted to detect the rotary motion of the arm typically by an encoder. It then locates the front end of the probe on the basis of the rotary motion. Thus, as in the case of an optical sensor system adapted to detect infrared rays, the front end of the probe can be located in the coordinate system 30 for the real space.

Thus, the positions $(x_W(i), y_W(i), z_W(i))$ ($i=1, 2, \ldots, n$) of the markers detected in the above described Step S12 are located in the coordinate system 30 for the real space by the probe sensor.

Now, Step S14 in FIG. 13 will be discussed below.

It should be noted that not all the markers detected in Step S12 are located in Step S13. Therefore, in this step, the markers that are detected in both Step S12 and Step S13 are rearranged to clarify their correspondence and expressed in terms of coordinate values of $(x_P(k), y_P(k), z_P(k))$ and
$(x_W(k), y_W(k), z_W(k))$,
where $k=1, 2, \ldots, n$.

In Step S14, then the coordinates of the coordinate system 29 for the image for examination and those of the coordinate system 30 for the real space are registered. In other words, the coordinate transformation parameters for transforming the coordinate system 29 for the image for examination into the coordinate system 30 for the real space are computationally determined. In mathematical terms, it is an operation of determining $_WH_P$ or (R, t) expressed respectively by formulas below $$\begin{bmatrix} x_W(k) \\ y_W(k) \\ z_W(k) \\ 1 \end{bmatrix} = {_WH_P} \begin{bmatrix} x_P(k) \\ y_P(k) \\ z_P(k) \\ 1 \end{bmatrix} \text{ or } \begin{bmatrix} x_W(k) \\ y_W(k) \\ z_W(k) \end{bmatrix} = R \begin{bmatrix} x_P(k) \\ y_P(k) \\ z_P(k) \end{bmatrix} + t$$

If the vector of the center of gravity of the markers in the two coordinate systems are expressed respectively by $(x_W^{mean}, y_W^{mean}, z_W^{mean})$ and $(x_P^{mean}, y_P^{mean}, z_P^{mean})$, the equations below hold true so that the translation vector and the rotary matrix can be determined independently by using respective formulas.

$$\begin{bmatrix} x_W(k) - x_W^{mean} \\ y_W(k) - y_W^{mean} \\ z_W(k) - z_W^{mean} \end{bmatrix} = R \begin{bmatrix} x_P(k) - x_P^{mean} \\ y_P(k) - y_P^{mean} \\ z_P(k) - z_P^{mean} \end{bmatrix} \quad t = \begin{bmatrix} x_W^{mean} \\ y_W^{mean} \\ z_W^{mean} \end{bmatrix} - R \begin{bmatrix} x_W^{mean} \\ y_W^{mean} \\ z_W^{mean} \end{bmatrix}$$

The above equations may be solved for $i=1, 2, 3$ by the quaternion technique, which will not be described any further because it is described in detail in B. K. P. Horn, "Closed-form solution of absolute orientation using unit quaternions", Journal of Optical Society of America A, Vol. 4, No. 4, 1987, pp. 629–642.

It will be understood that, once R, t are determined, homogeneous transformation matrix $_WH_P$ can be computed with ease. More specifically, if the elements of R are $r_{ij}$ and those of t are $(t_x, t_y, t_z)$, they can be expressed as follow.

$$_WH_P = \begin{bmatrix} R & t \\ 0 & 1 \end{bmatrix} = \begin{bmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{bmatrix}$$

Now, Step S15 will be discussed below.

Once the coordinates of the coordinate system 29 for the image for examination and those of the coordinate system 30 for the real space are registered in Step S14, the coordinate transformation parameters for transforming the coordinate system 29 for the image for examination into the coordinate system 30 for the real space are obtained. Then, the surgical instrument 28 can be navigated by detecting the position/orientation of the surgical instrument 28 in the coordinate system 30 for the real space. This process is described earlier and hence will not be described here any further.

As described above in detail, the processing operation of operative calibration that has hitherto been a cumbersome process can now be carried out with easy by using the first embodiment of reference frame according to the invention. More specifically, the first embodiment provides the following advantages.

1) The reference frame 1 is structurally stable and reliable when used during the surgical operation.
2) The reference frame 1 can be removed with ease after taking tomographic images of target portion of surgical operation and reliably restored to the original position prior to the surgical operation.

3) The markers of the reference frame 1 can be detected with ease from the tomographic images of the site of the surgical operation and their correspondence to the respective markers on the frame 1 fitted to the subject 27 of surgical operation can be confirmed with ease.

$2^{nd}$ Embodiment

Method of Utilizing a Secondary Marker Plate

Now, the second embodiment of the invention will be described.

While the first embodiment of the invention is described in terms of a scene where the reference frame 1 is used directly during the surgical operation, the second embodiment provides an advantage that the reference frame 1 does not need to be removed during the surgical operation and the 3-D position sensor 24 can effectively be used for detecting the markers in such a way that, if the subject 27 moves during the surgical operation, it follows the motion of the subject and hence the coordinates of both the coordinate system 29 for the image for examination and the coordinate system 30 for the real space are registered to reliably reflect the motion.

As described above by referring to the first embodiment, an optical sensor system adapted to detect infrared rays can be used as the 3-D position sensor 24 for detecting the markers. Such a system can not only detect markers but also be used for other purposes. To be more accurate, a plate equipped with a plurality of IR emitting diodes (LEDs) is used and the coordinate system defined by the plate is used as provisional reference coordinate system. In other words, the plate is rigidly secured to the body of the subject 27 so that the movement of the subject 27 is cancelled by the movement of the plate and the movement of the surgical instrument 28 is defined in terms of a corresponding relative movement of the plate and the surgical instrument. With this technique, the relative positional relationship between the surgical instrument as defined in terms of the coordinate system 31 for the surgical instrument 28 and the subject 27 as defined in terms of the coordinate system 29 for the image for examination can be detected as a function of time at any time during the surgical operation.

Figure 17:
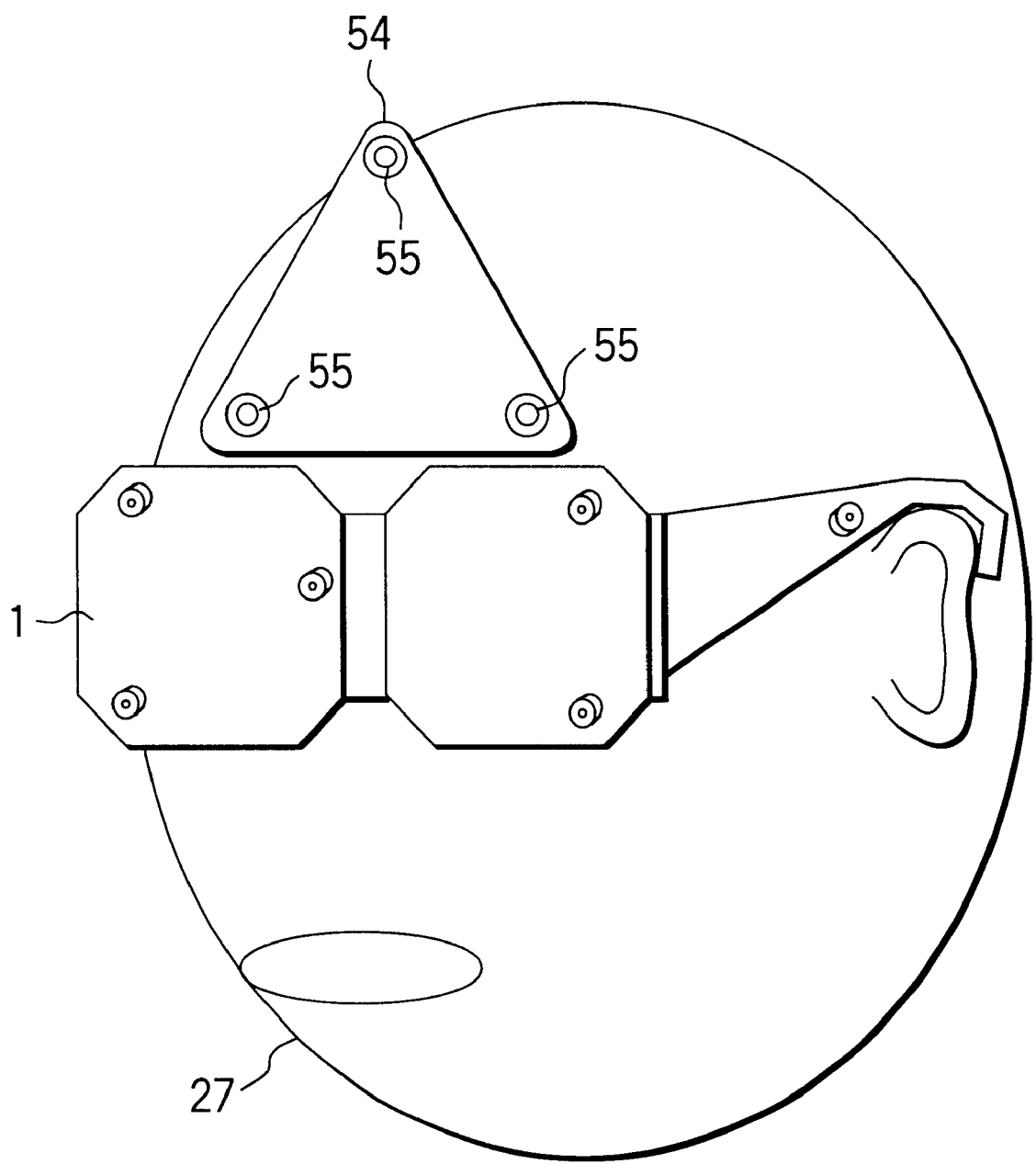
FIG. 17 is a schematic illustration of a second embodiment of a reference frame according to the invention, showing its basic configuration.

Now, the embodiment will be described in greater detail. FIG. 17 is a schematic illustration of a second embodiment of reference frame according to the invention, showing its basic configuration. Referring to FIG. 17, the reference frame 1 is rigidly fitted to the subject 27 along with a secondary marker plate 54 that is independent from the reference frame 1. The secondary marker plate 54 is provided with secondary markers 55. More specifically, a plurality of secondary markers 55 that can be optically recognized by the 3-D position sensor 24 are provided. The secondary markers 55 may be IR emitting diodes (LEDs).

Figure 18:
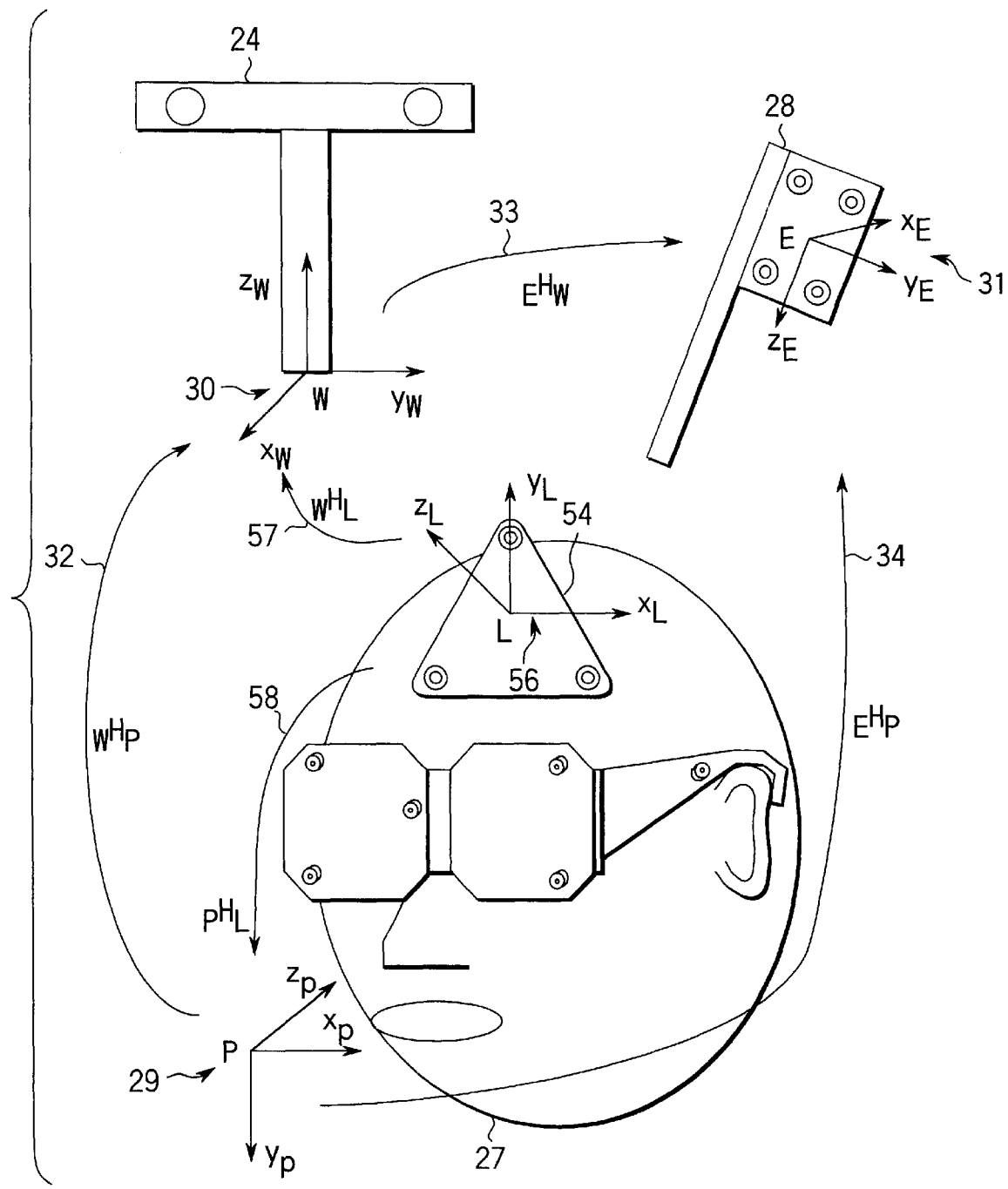
FIG. 18 is a schematic illustration of a possible relationship of different coordinate systems when a secondary marker plate is used.

FIG. 18 is a schematic illustration of a possible relationship of different coordinate systems when a secondary marker plate 54 is used. Unlike the coordinate systems and the coordinate transformation of FIG. 7, a coordinate system 56 for the secondary marker plate is defined for the secondary marker plate 54 and subsequently the coordinate transformation 57 from the coordinate system 56 for the secondary marker plate to the coordinate system 30 for the real space is defined in this embodiment. The coordinate transformation parameters to be used for the coordinate transformation 57 are determined by detecting the positions of the secondary markers 55 on the secondary marker plate 54 by the 3-D position sensor 24. Then, the coordinate transformation 58 from the coordinate system 56 for the secondary marker plate 54 to the coordinate system 29 for the image for examination is also defined.

The operative calibration of this embodiment differs from that of the first embodiment illustrated in FIG. 13 in terms of Step S13 and Step S14.

More specifically, Step S13 of this second embodiment includes the above described Step S14.

Now, Step S13 of this embodiment will be discussed in detail below.

Figure 19:
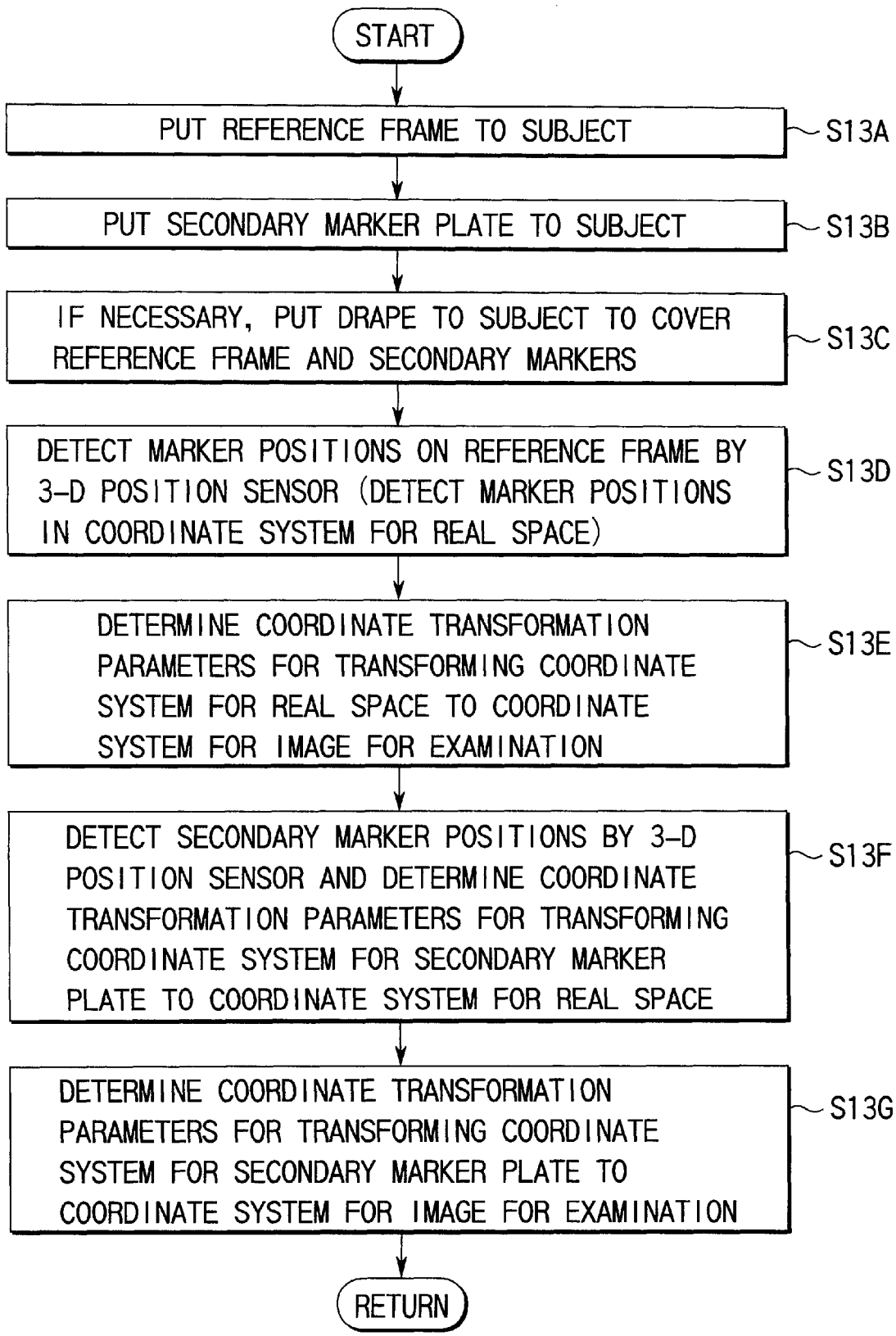
FIG. 19 is a flow chart of the step of detecting a marker in a real space containing a subject of examination in FIG. 13 when conducted by using the second embodiment of the invention.

FIG. 19 is a flow chart of Step S13 of the operative calibration in FIG. 13 when conducted by using the second embodiment of the invention.

Referring to FIG. 19, firstly, the reference frame 1 is fitted to the subject 27 (Step S13A). Then, the secondary marker plate 54 is fitted to the subject 27 (Step S13B). Subsequently, a drape is put on the reference frame 1 and the secondary marker plate 54 if necessary to produce a clean environment (Step S13C). Care should be taken when placing the drape so as not to move the reference frame 1.

Then, the markers on the reference frame 1 are detected by the 3-D position sensor 24 to obtain coordinate values of the markers in the coordinate system 30 for the real space (Step S13D). Thereafter, the coordinate transformation parameters for transforming the coordinate system 30 for the real space into the coordinate system 29 for the image for examination are determined (Step S13E). Subsequently, the coordinate transformation parameters for transforming the coordinate system 56 for the secondary marker plate into the coordinate system 30 for the real space are determined by detecting the positions of the secondary markers 55 in the coordinate system 30 for the real space by the 3-D position sensor 24. Finally, the coordinate transformation parameters for transforming the coordinate system 56 for the secondary marker plate into the coordinate system 29 for the image for examination are determined (Step 513G).

Now, Steps S13A through 13G will be discussed below in greater detail.

Firstly, in Step S13A, the reference frame 1 is put on the subject 27 in a manner as described above by referring to the first embodiment.

Step S13B will be discussed further below.

In Step S13B, the secondary marker plate 54 is fitted to the subject 27. The secondary marker plate 54 must be put on the subject at a place where it can be easily and securely fitted to the latter and also easily detected by the 3-D position sensor 24 such as the forehead of the subject 27 as shown in FIG. 17. When fitting the secondary marker plate 54 to the subject 27, a filling material that hardens with time may also be used to secure the plate 54 onto the subject 27 as described above by referring to the first embodiment.

Now, Step S13C will be discussed further below.

In Step S13C, a drape is placed on the reference frame 1 and the secondary marker plate 54 if necessary to produce a clean environment for the surgical operation. Care should be taken when placing the drape so as not to move the reference frame 1. This step is identical with that of the above described first embodiment.

Now, Step S13D will be discussed further below.

In Step S13D, the markers on the reference frame 1 are detected by the 3-D position sensor 24 in a manner exactly as described above for the first embodiment. It may be needless to say that the positions of the markers 5 through 11 on the reference frame 1 are defined in terms of the coordinate system 30 for the real space.

Now, Step S13E will be discussed further below.

In Step S13E, the coordinate transformation parameters for transforming the coordinate system 30 for the real space into the coordinate system 29 for the image for examination are determined in a manner exactly as described above for the first embodiment.

Now, Step S13F will be discussed further below.

Since the secondary marker plate 54 is rigidly secured in position, the positions of the secondary markers 55 in the coordinate system 56 for the secondary marker plate can be detected and defined in advance. Assume that a total of m secondary markers 55 are provided at respective positions $(x_L(i), y_L(i), z_L(i))$ (i=1, 2, ..., m) in the coordinate system 56 for the secondary marker plate.

Then, in Step S13F, the secondary markers 55 are detected by the 3-D position sensor 24 in the coordinate system 30 for the real space in a manner exactly as described above for the first embodiment. The positions of the secondary markers 55 as detected by the 3-D position sensor 24 should be defined in terms of the coordinate system 30 for the real space as $(x_W(i), y_W(i), z_W(i))$ (i=1, 2, ..., m). Then, if the coordinate transformation parameters for transforming the coordinate system 56 for the secondary marker plate into the coordinate system 30 for the real space are expressed by $_WH_L$, the equation below holds true.

$$\begin{bmatrix} xW^{(i)} \\ yW^{(i)} \\ zW^{(i)} \\ 1 \end{bmatrix} = {^W}H_L \begin{bmatrix} xL^{(i)} \\ yL^{(i)} \\ zL^{(i)} \\ 1 \end{bmatrix} \quad (i=1,2,\ldots,m)$$

The coordinate transformation parameters for transforming the coordinate system 56 for the secondary marker plate into the coordinate system 30 for the real space can be determined by detecting $_WH_L$ that satisfy the requirement of the above equation. Since the technique described above for Step S14 of the first embodiment can also be used here, it will not be described here any further. Step S13F is terminated when the coordinate transformation parameters are determined.

Now, Step S13G will be discussed further.

In Step S13G, the coordinate transformation parameters for transforming the coordinate system 56 for the secondary marker plate into the coordinate system 29 for the image for examination are determined by utilizing the two coordinate transformations performed in Steps S13E and S13F above. More specifically, if the coordinate transformation parameters for transforming the coordinate system 30 for the real space into the coordinate system 29 for the image for examination as obtained in Step S13E are expressed by $_PH_W$ and the coordinate transformation parameters for transforming the coordinate system 56 for the secondary marker plate into the coordinate system 30 for the real space as obtained in Step S13F are expressed by $_WH_L$, the coordinate transformation parameters $_PH_L$ for transforming the coordinate system 56 for the secondary marker plate into the coordinate system 29 for the image for examination can be determined by way of a multiplication of matrixes of 4 rows and 4 columns as shown below.

$$_PH_L = {_PH_W} {_WH_L}$$

Figure 20:
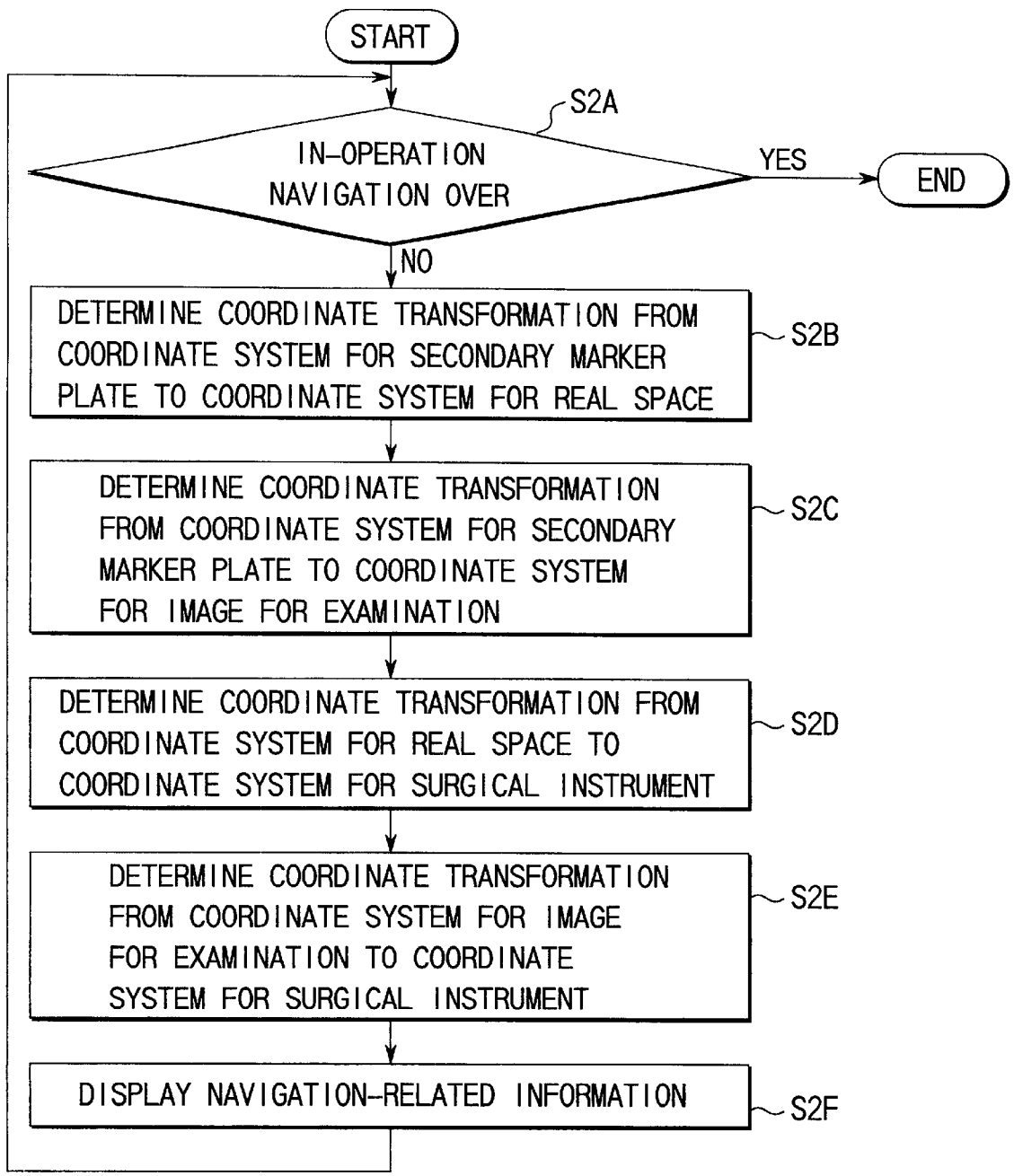
FIG. 20 is a flow chart of the in-operation navigation processing step of FIG. 6, illustrating the basic steps thereof when conducted by using the second embodiment of the invention.

The in-operation navigation processing of the second embodiment proceeds in a manner as illustrated by the flow chart of FIG. 20.

Referring to FIG. 20, firstly, it is checked if the in-operation navigation processing is to be terminated or not (Step S2A) and, if it is found that the in-operation navigation processing is not to be terminated, the coordinate transformation parameters $_WH_L$ for defining the coordinate transformation from the coordinate system 56 for secondary marker plate into the coordinate system 30 for the real space are determined (Step S2B).

Subsequently, the coordinate transformation parameters $_PH_L$ for defining the coordinate transformation from the coordinate system 56 for the secondary marker plate into the coordinate system 29 for the image for examination are determined by the 3-D position sensor 24 defined in the coordinate system 30 for the real space (Step S2C). More specifically, if the secondary markers 55 are IR emitting diodes (LEDs), the positions of the IR emitting diodes are detected by the 3-D position sensor 24 and the coordinate transformation parameters $_PH_L$ for transforming the coordinate system 56 for the secondary marker plate into the coordinate system 29 for the image for examination are determined by using the information on the arrangement of the IR emitting diodes.

Then, the coordinate transformation parameters $_EH_W$ for defining the coordinate transformation from the coordinate system 30 for the real space to the coordinate system 31 for the surgical instrument are computationally determined (Step S2D). To do this, the three-dimensional position/attituide of the surgical instrument 28 is detected by the 3-D position sensor 24 arranged in the real space.

Subsequently, the coordinate transformation parameters $_EH_P$ for defining the coordinate transformation from the coordinate system 29 for the image for examination to the coordinate system 31 for the surgical instrument are computationally determined (Step S2E) by utilizing the outcome of the above Steps S2B through S2D. More specifically, they can be determined by way of a multiplication of matrixes of 4 rows and 4 columns as shown below.

$$_EH_P = {_EH_W} {_WH_L} {_LH_P} = {_EH_W} {_WH_L} ({_PH_L})^{-1}$$

Finally, (1) the position of the surgical instrument 28 in the coordinate system 29 for the image for examination and (2) the position of the site of operation as transferred from the coordinate system 29 for the image for examination to the coordinate system 31 for the surgical instrument are computationally determined by using the coordinate transformation 34 from the coordinate system 29 for the image for examination to the coordinate system 31 for the surgical instrument to obtain navigation-related information required for the surgical operation, which information is then displayed on the display screen of the monitor 26 exactly as described above by referring to the first embodiment.

As described above, since the positional relationship between the coordinate system 29 for the image for examination and the coordinate system 56 for the secondary marker plate is invariable in the second embodiment, the movement, if any, of the subject 27 that shifts the coordinate system 29 for the image for examination relative to the coordinate system 30 for the real space can be cancelled by observing the movement in the coordinate system 56 for the secondary marker plate. Thus, it is possible to realize a coordinate transformation 34 from the coordinate system 29 for the image for examination into the coordinate system 31 for the surgical instrument in order to navigate the surgical instrument if the body of the subject 27 moves.

3rd Embodiment
The Use of Removable Markers

Now, the third embodiment of the invention will be described.

Markers that can be detected by way of both MRI images and CT images are described above by referring to the first embodiment and a technique of operative navigation utilizing a marker plate 54 provided with secondary markers 55 that are IR emitting diodes is described by referring to the second embodiment. However, the second embodiment needs a marker plate 54 separated from the reference frame 1 because it is difficult to obtain an MRI image for medical examination by using metal parts such as IR emitting diodes (LEDs) fitted to the reference frame 1.

Therefore, the reference frame 1 of the third embodiment is so designed that, if necessary, metal markers such as IR emitting diodes (LEDs) or a marker plate can be removably fitted to the reference frame 1.

Figure 21:
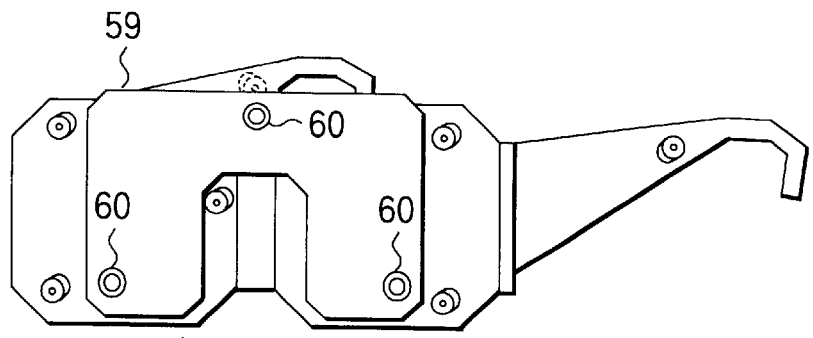
FIG. 21 is a schematic illustration of a third embodiment of a reference frame according to the invention and using a removable secondary marker plate.

FIG. 21 is a schematic illustration of the third embodiment of reference frame according to the invention that uses a removable secondary marker plate 59. Referring to FIG. 21, a secondary marker plate 59 is provided with secondary markers 60 and removably fitted to the reference frame 1. When the secondary marker plate 59 is fitted to the reference frame 1, the latter can be accurately placed on the subject 27.

Assume that the secondary marker plate 59 is fitted to the reference frame 1 as shown in FIG. 21 and the positions of the secondary markers on the secondary marker plate 59 are expressed by $(x_L(i), y_L(i), z_L(i))$ in terms of the coordinate system for the secondary marker plate, while the positions of the markers on the reference frame 1 are expressed by $(x_M(j), y_M(j), z_M(j))$ in a similar coordinate system. Then, the coordinate transformation parameters $_WH_L$ for transforming the coordinate system for the secondary marker plate into the coordinate system for the real space can be determined by detecting the positions of the secondary markers 60 on the secondary marker plate 59 by the 3-D position sensor 24 whose position is defined by the coordinate system for the real space. Then, the positions $(x_W(j), y_W(j), z_W(j))$ of the markers on the reference frame 1 in the coordinate system for the real space can be determined by the equation below.

$$\begin{bmatrix} x_W(j) \\ y_W(j) \\ z_W(j) \\ 1 \end{bmatrix} = W^H L \begin{bmatrix} x_M(j) \\ y_M(j) \\ z_M(j) \\ 1 \end{bmatrix}$$

In other words, the positions of the markers on the reference frame 1 in the coordinate system for the real space can be determined without detecting them by a probe.

Thus, by using a removable secondary marker plate 59, the positions of the markers 60 on the secondary marker plate 59 can be directly detected by a 3-D position sensor 24 and defined in terms of the coordinate system for the real space.

Since the operative calibration of this embodiment is otherwise identical with the that of the second embodiment, it will not be described here any further.

While a secondary marker plate 59 is used in the third embodiment, the secondary markers 60 do not necessary have to be placed on the secondary marker plate 59. For example, the secondary markers may be so arranged that they can be directly driven into the reference frame 1. With such an arrangement, the positions of the secondary markers can be defined accurately on the reference frame 1. In other words, as described above, the positions of the markers on the reference frame 1 in the coordinate system for the real space can be determined without detecting them by a probe to simply the process of operative calibration.

As described above, with the third embodiment designed to utilize removable secondary markers 60 and a secondary marker plate 59, the coordinates can be registered in terms of the coordinate system for the image for examination and the coordinate system for the real space without detecting the markers on the reference frame 1 by a probe. Thus, the third embodiment provides advantages of 1) simplified operative calibration and
2) simplified maintenance of a clean environment due to the nonuse of a probe.

4$^{th}$ Embodiment

Now, the fourth embodiment of the invention will be described below.

Figure 22:
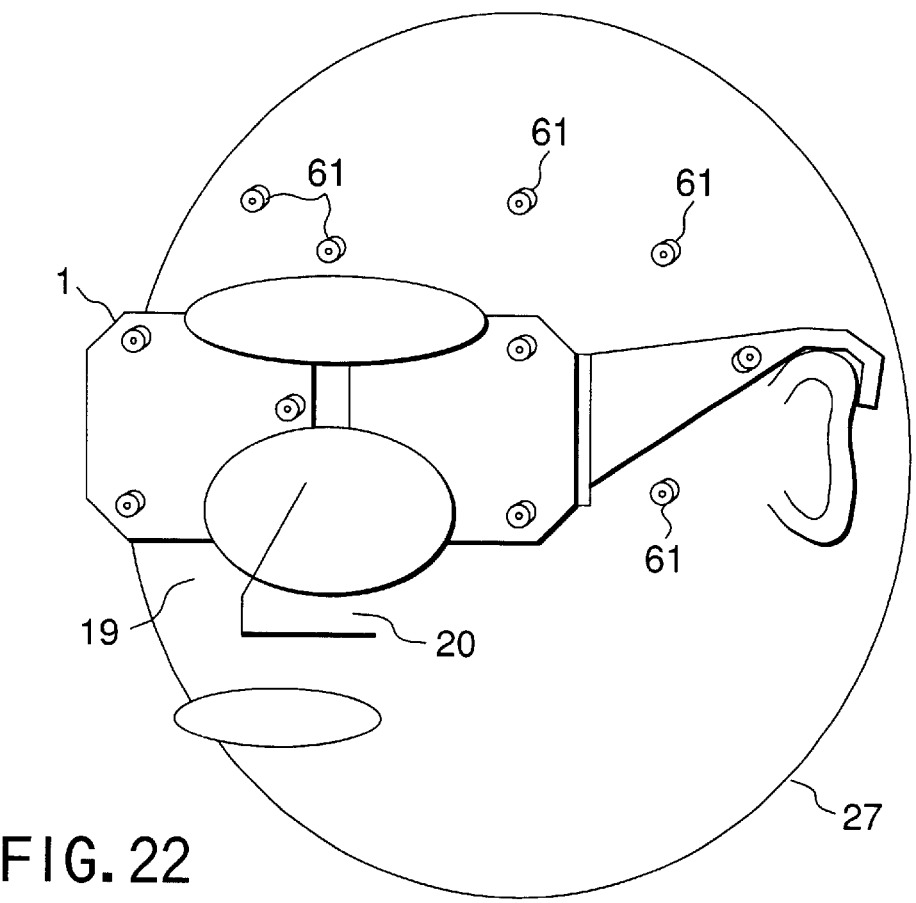
FIG. 22 is a schematic illustration of a fourth embodiment of a reference frame according to the invention and being used on a subject of examination with secondary markers.

With the fourth embodiment, a plurality of secondary markers 61 are fitted to the surface of the body of the subject 27 in areas other than the reference frame 1 in a manner as shown in FIG. 22.

Figure 23:
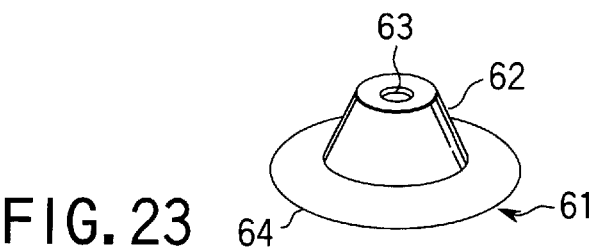
FIG. 23 is a schematic perspective view of a secondary marker that can be used with the fourth embodiment of reference frame according to the invention.

As shown in FIG. 23, each of the secondary markers 61 that are fitted to the subject has a secondary marker main body 62, a probe receiving recess 63 providing easy access to the probe and an adherent section 64 that can easily be made to adhere to the surface of the body of the subject.

Figure 24:
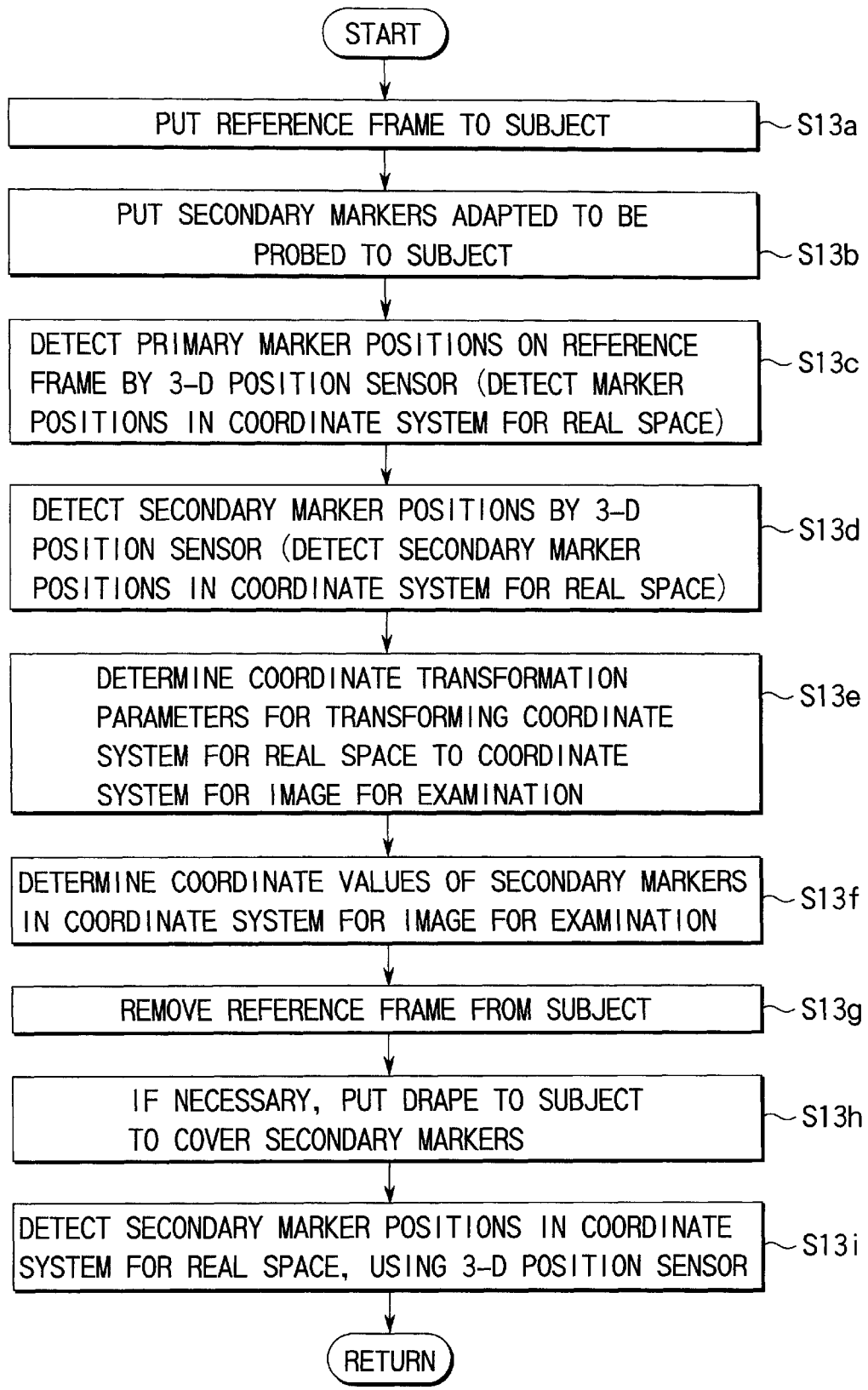
FIG. 24 is a flow chart of the step of detecting a marker in a real space containing a subject of examination in FIG. 13 when conducted by using the fourth embodiment of the invention.

With the fourth embodiment, the Steps S13 and S14 proceed in a manner as described below by referring to FIG. 24.

Firstly, the reference frame 1 is fitted to the subject (Step S13a). More specifically, the reference frame 1 that is used to take tomographic images of the subject 27 is once again placed on the subject in Step S13a. It is necessary to make sure that the reference frame 1 is accurately in position. A filling material 18, 19 that hardens with time may effectively be used to securely place the reference frame 1 in position.

Then, secondary markers 61 that can be detected by a probe are fitted to the subject 27 (Step S13b). Note that the secondary markers 61 are fitted to the surface of the body of the subject as shown in FIG. 22 at positions that can easily be detected by a sensor probe for the surgical operation to be performed on the subject. The number of secondary markers 61 needs to be three or more than three.

Then, the positions of the :markers (primary markers) 5 through 11 on the reference frame 1 are detected by the 3-D position sensor to determine their coordinates in the coordinate system 30 for the real space (regardless if they are in a clean environment or not) (Step S13c). Assume that the coordinates of the primary markers are expressed by $(x_W(i), y_W(i), z_W(i))$ $(i=1, 2, \ldots, n)$.

Thereafter, the positions of the secondary markers 61 are also detected by the 3-D position sensor to determine their coordinates in the coordinate system 30 for the real space (regardless if they are in a clean environment or not) (Step S13d). Assume that the coordinates of the secondary markers are expressed by $(X_{W2}(j), Y_{W2}(j), Z_{W2}(j))$.

Then, the coordinate transformation parameters for transforming the coordinate system 30 for the real space into the coordinate system 29 for the image for examination are determined (Step S13e). More specifically, the coordinate transformation parameters $_PH_W$ for transforming the coordinate system 30 for the real space into the coordinate system 29 for the image for examination are determined by using the coordinate pairs $(X_P(k), Y_P(k), Z_P(k))$, $(X_W(k), Y_W(k), Z_W(k))$ for the positions of the primary markers detected on the reference frame 1 by way of both the coordinate system 30 for the real space and the coordinate system 29 for the image for examination.

In mathematical terms, it is an operation of determining $_PH_W$ or $(R, t)$ expressed respectively by formulas below $$\begin{bmatrix} x_P(k) \\ y_P(k) \\ z_P(k) \\ 1 \end{bmatrix} = {}_pH_W \begin{bmatrix} x_W(k) \\ y_W(k) \\ z_W(k) \\ 1 \end{bmatrix} \text{ or } \begin{bmatrix} x_P(k) \\ y_P(k) \\ z_P(k) \end{bmatrix} = R \begin{bmatrix} x_W(k) \\ y_W(k) \\ z_W(k) \end{bmatrix} + t$$

If the vector of the center of gravity of the primary markers in the two coordinate systems are expressed respectively by ($X_W$mean, $Y_W$mean, $Z_W$mean) and ($X_P$mean, $Y_P$mean, $Z_P$mean), the equations below hold true so that the translation vector and the rotary matrix can be determined independently by using respective formulas.

$$\begin{bmatrix} x_P(k) - x_P^{mean} \\ y_P(k) - y_P^{mean} \\ z_P(k) - z_P^{mean} \end{bmatrix} = R \begin{bmatrix} x_W(k) - x_W^{mean} \\ y_W(k) - y_W^{mean} \\ z_W(k) - z_W^{mean} \end{bmatrix}$$

$$t = \begin{bmatrix} x_P^{mean} \\ y_P^{mean} \\ z_P^{mean} \end{bmatrix} - R \begin{bmatrix} x_W^{mean} \\ y_W^{mean} \\ z_W^{mean} \end{bmatrix}$$

The above equations may be solved for i=1, 2, 3 by the quaternion technique.

It will be understood that, once R, t are determined, homogeneous transformation matrix $_pH_W$ can be computed with ease. More specifically, if the elements of R are $r_{ij}$ and those of t are ($t_x$, $t_y$, $t_z$), they can be expressed as follow.

$$_pH_W = \begin{bmatrix} R & t \\ 0 & 1 \end{bmatrix} = \begin{bmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{bmatrix}$$

Then, the coordinate values of the positions of the secondary markers 61 in the coordinate system 29 for the image for examination are determined (Step S13f). The obtained coordinate values are as those of the secondary markers. More specifically, the coordinate values ($X_{P2}(j)$, $Y_{P2}(j)$, $Z_{P2}(j)$) of the secondary markers in the coordinate system 29 for the image for examination are determined by the equation below that utilizes the coordinate transformation parameters $_pH_W$ for transforming the coordinate system 30 for the real space into the coordinate system 29 for the image for examination as determined in Step S13e above.

$$\begin{bmatrix} x_{P2}(j) \\ y_{P2}(j) \\ z_{P2}(j) \\ 1 \end{bmatrix} = {}_pH_W \begin{bmatrix} x_{W2}(j) \\ y_{W2}(j) \\ z_{W2}(j) \\ 1 \end{bmatrix}$$

Subsequently, the reference frame 1 is removed from the body of the subject 27 if necessary (Step S13g). Note, however, the secondary markers 61 are not removed in this step (and the reference frame 1 does not necessarily have to be removed).

With the above process, the use of the reference frame 1 is over and all the necessary positional information is obtained by detecting the positions of the secondary markers.

Thereafter, if necessary, a drape is put on the subject 27 who is still carrying the secondary markers 61 in order to produce a clean environment necessary for the surgical operation (Step S13h).

Then, the positions of the secondary markers 61 in the coordinate system 30 for the real space are detected by the 3-D position sensor 24 (Step S13i). Assume that the coordinates of the secondary markers are expressed by ($X_{W2}(J)$, $Y_{W2}(J)$, $Z_{W2}(J)$).

Thereafter, the processing operation proceeds to Step S14, where the coordinates of the coordinate system 29 for the image for examination and those of the coordinate system 30 for the real space are registered by utilizing the positions of the secondary markers 61 in the image for examination and those in the real space.

More specifically, the coordinate transformation parameters $_pH_W'$ for transforming the coordinate system 30 for the real space into the coordinate system 29 for the image for examination are determined by using the coordinate pairs ($X_{P2}(J)$, $Y_{P2}(J)$, $Z_{P2}(J)$), ($X_{W2}(J)$, $Y_{W2}(J)$, $Z_{W2}(J)$) for the positions of the secondary markers detected in both the coordinate system 29 for the image for examination and the coordinate system 30 for the real space.

Differently stated, all the secondary markers registered by the coordinate system 29 for the image for examination in Step S13 may not necessarily be detected by the 3-D position sensor 24 in the operating room because of the drape put on the markers. Therefore, in Step S14, the coordinate transformation parameters for transforming the coordinate system 30 for the real space into the coordinate system 29 for the image for examination are determined by using only the secondary markers that provide corresponding coordinate values between the two operations of detecting them.

Assume that positions of the secondary markers that provide corresponding coordinate values are expressed by ($X_{P2}(k)$, $Y_{P2}(k)$, $Z_{P2}(k)$), ($X_{P2}(k)$, $Y_{W2}(k)$, $Z_{W2}(k)$) (k=1, 2, . . . , n). Then, in mathematical terms, the coordinate transformation parameters $_pH_W'$ can be determined by formulas below so that both the coordinates of the coordinate system 29 for the image for examination and those of the coordinate system 30 for the real space can now be registered.

$$\begin{bmatrix} x_{P2}(k) \\ y_{P2}(k) \\ z_{P2}(k) \\ 1 \end{bmatrix} = {}_pH_W' \begin{bmatrix} x_{W2}(k) \\ y_{W2}(k) \\ z_{W2}(k) \\ 1 \end{bmatrix} \text{ or } \begin{bmatrix} x_{P2}(k) \\ y_{P2}(k) \\ z_{P2}(k) \end{bmatrix} = R' \begin{bmatrix} x_{W2}(k) \\ y_{W2}(k) \\ z_{W2}(k) \end{bmatrix} + t'$$

As described above in detail, the processing operation of operative calibration that has hitherto been a cumbersome process can now be carried out with easy by using the first embodiment of reference frame according to the invention. More specifically, the operative calibration is carried out by using both the reference frame 1 and the secondary markers 61 at the same time to make it no longer necessary to use the reference frame 1 during the surgical operation. Since the secondary markers 61 do not obstruct the surgical operation, the use of this embodiment is highly acceptable to the patient from the viewpoint of operative navigation.

Thus, in the process of operative calibration of defining the position/orientation of the image taken for examination and that of the patient by the reference frame of the fourth embodiment that is rigidly secured to the patient, markers that are not fitted onto the reference frame are placed on the patient. Then, the positions of the markers are defined in terms of the coordinate system 29 for the image for examination by the reference frame and then detected in the coordinate system 30 for the real space where the patient is found in order to register the coordinates of the coordinate system 29 for the image for examination and those of the coordinate system 30 for the real space. This embodiment can be flexibly adapted to the selected surgical operation as it effectively utilizes both the primary markers put on the reference frame 1 and the secondary markers 61 that are not put on the reference frame 1.

5<sup>th</sup> Embodiment

Now, the fifth embodiment of the invention will be described below.

While the fourth embodiment utilizes all the secondary markers 61 that are registered and detected to determine the coordinate transformation parameters for transforming the coordinate system 30 for the real space into the coordinate system 29 for the image for examination, some of the secondary markers 61 can be partly deformed as a result of the use of a drape.

The fifth embodiment is so adapted that any secondary markers that are recognized to be partly deformed are eliminated from the registration when determining the coordinate transformation parameters for transforming the coordinate system 30 for the real space into the coordinate system 29 for the image for examination.

Figure 25:
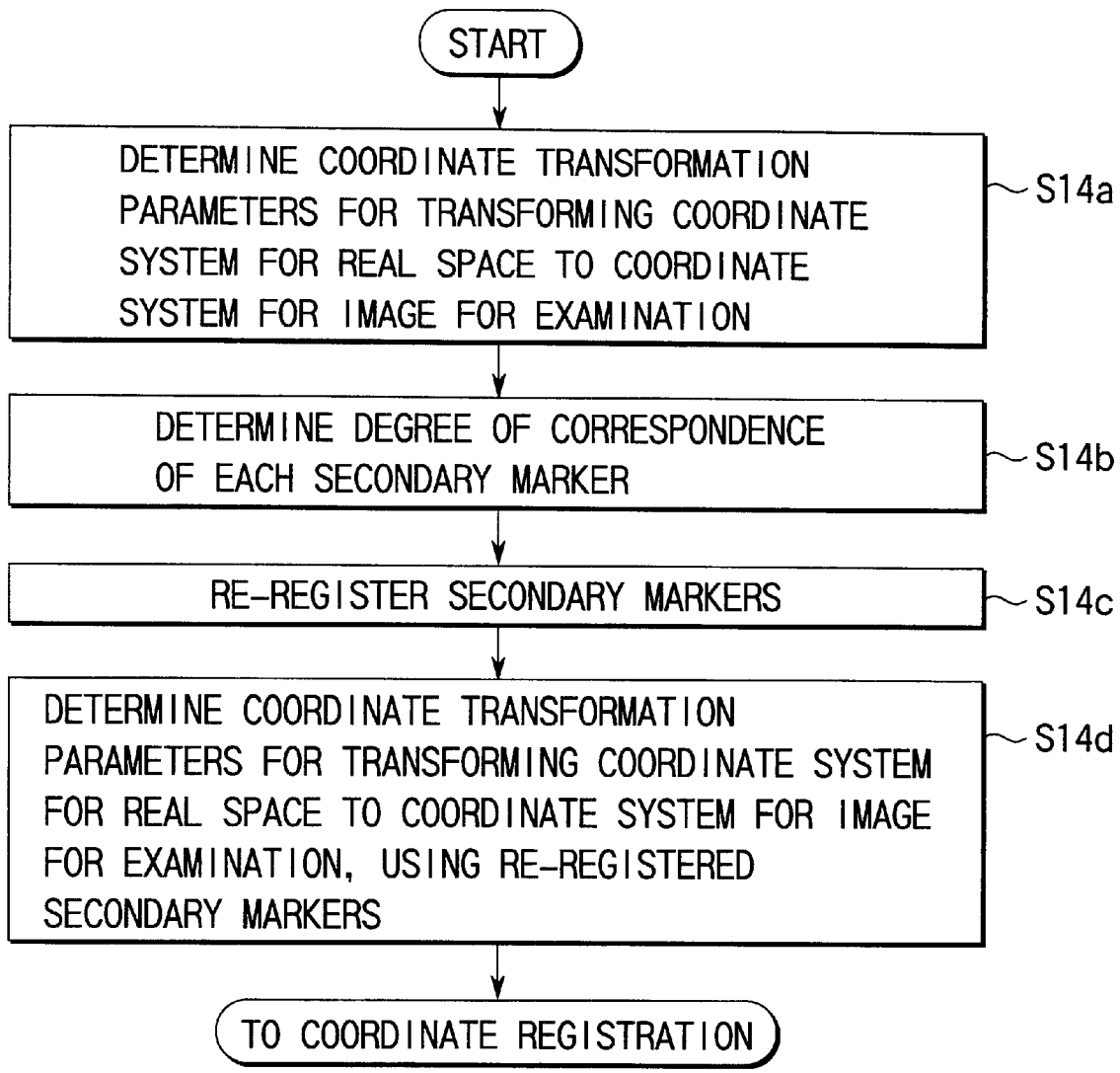
FIG. 25 is a flow chart of the step of coding the image obtained for examination and the subject of examination in FIG. 13 when conducted by using a fifth embodiment of the invention.

More specifically, the operation as described below by referring to FIG. 25 is added to Step S14 of the fourth embodiment to eliminate the secondary markers in question from the registration.

Assume that the positions of the secondary markers registered in Step S13 described above by referring to the fourth embodiment and detected by the 3-D position sensor 24 are expressed by coordinates $(X_{P2}(k), Y_{P2}(k), Z_{P2}(k))$ in the coordinate system 29 for the image for examination and coordinates $(X_{W2}(k), Y_{W2}(k), Z_{W2}(k))$ in the coordinate system 30 for the real space. Then, firstly, the coordinate transformation parameters $_PH_W'$ for transforming the coordinate system 30 for the real space into the coordinate system 29 for the image for examination are determined by using all the coordinate values (Step S14a). Assume that the coordinate transformation parameters $_PH_W'$ are expressed by the formula below. This technique is same as the one described above by referring to the fourth embodiment and hence will not be described here any further.

$$_PH_W' = \begin{bmatrix} R' & t' \\ 0 & 1 \end{bmatrix}$$

Then, the degree of correspondence e(k) (k=1, 2, ..., N) is determined for each of the markers by the formula below, using the coordinate transformation parameters $_PH_W'$, R', t' (Step S14b).

$$\begin{bmatrix} e_x(k) \\ e_y(k) \\ e_z(k) \end{bmatrix} = R' \begin{bmatrix} x_{W2}(k) \\ y_{W2}(k) \\ z_{W2}(k) \end{bmatrix} + t' \begin{bmatrix} x_{P2}(k) \\ y_{P2}(k) \\ z_{P2}(k) \end{bmatrix}$$

$$e(k) = \sqrt{(e_x(k))^2 + (e_y(k))^2 + (e_z(k))^2}$$

Then, each of the secondary markers is processed for re-registration on the basis of the degree of correspondence e(k). A marker k with e(k)<threshold is judged to be placed in position without problem and hence is re-registered, whereas a marker k with e(k) threshold is judged to have problem and hence is eliminated (Step S14c). Note that "threshold" above is a predetermined constant (and the number of re-registered secondary markers is three or greater than three).

Assume that the coordinates of the re-registered secondary markers are again $(X_{P2}(k), Y_{P2}(k), Z_{P2}(k)), (X_{W2}(k), Y_{W2}(k), Z_{W2}(k))$. Then, the coordinate transformation parameters $_PH_W'$ for transforming the coordinate system 30 for the real space into the coordinate system 29 for the image for examination are determined by using all the coordinate values as in Step S14a (Step S14d). Now, both the coordinates of the coordinate system 29 for the image for examination and those of the coordinate system 30 for the real space can now be registered.

With the above steps, it is possible to determine the coordinate transformation parameters with an enhanced degree of reliability to improve the reliability of the operative calibration.

In short, with the fifth embodiment, when that the detection of a marker position is accompanied by a degree of error higher than a given level, the marker is eliminated from the operation of the coordinate registration of the coordinate system 29 for the image for examination and the coordinate system 30 for the real space for the purpose of calibration to improve the reliability of the coordinate registration.

6<sup>th</sup> Embodiment
The Use of Secondary Markers Provided With a Position Sensor With the above described fourth and fifth embodiments, the three-dimensional positions of the secondary markers 61 are fitted to the subject 27 and then their positions are detected typically by a 3-D position sensor 24 such as a sensor probe to define their three-dimensional positions in the coordinate system 30 for the real space. While the above two embodiments provide the advantage that the secondary markers can wirelessly detected, the use of a 3-D position sensor 24 is indispensable for detecting them.

This sixth embodiment is designed to use an active marker plate to be fitted to the reference frame 1 and active secondary markers, each having an active type position sensor such as an LED buried in it, so that the operation of operative calibration can be conducted without relying on the use of a sensor probe.

Figure 26:
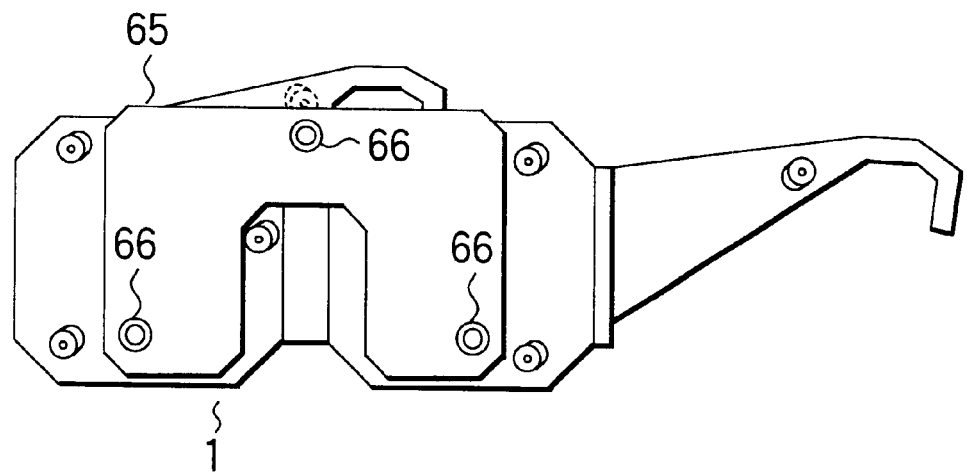
FIG. 26 is schematic illustration of a removable active marker plate being used with a sixth embodiment of a reference frame according to the invention.

FIG. 26 is schematic illustration of a removable active marker plate 65 being used with the sixth embodiment of reference frame according to the invention. As shown, the active marker plate 65 provided with active markers 66 is fitted onto the reference frame 1. The active marker plate 65 can be removably fitted to the reference frame 1 in a highly accurate way and, once it is fitted to the reference frame 1, it can restore its position on the latter if it is removed therefrom.

Assume that the active marker plate 65 is fitted to the reference frame 1 as shown in FIG. 26 and the positions of the active markers 66 on the active marker plate 65 are expressed by $(X_L(i), Y_L(i), Z_L(i))$ in terms of the coordinate system for the active marker plate, while the positions of the primary markers 5 through 11 on the reference frame 1 are expressed by $(X_M(J), Y_M(J), Z_M(J))$ in a similar coordinate system. Then, the coordinate transformation parameters $_WH_L$ for transforming the coordinate system for the active marker plate into the coordinate system for the real space can be determined by detecting the positions of the active markers 66 on the active marker plate 65 by the 3-D position sensor 24 whose position is defined by the coordinate system 30 for the real space. Then, the positions $(X_W(J), Y_W(J), Z_W(J))$ of the primary markers 5 through 11 on the reference frame 1 in the coordinate system 30 for the real space can be determined by the equation below, using the obtained coordinate transformation parameters.

$$\begin{bmatrix} x_W(j) \\ y_W(j) \\ z_W(j) \\ 1 \end{bmatrix} = {}_WH_L \begin{bmatrix} x_M(j) \\ y_M(j) \\ z_M(j) \\ 1 \end{bmatrix}$$

In other words, the positions of the primary markers 5 through 11 on the reference frame 1 in the coordinate system 30 for the real space can be determined without detecting them by a probe.

Thus, by using a removable active marker plate 65, the positions of the primary markers 5 through 11 in the coordinate system 30 for the real space can be computationally determined by directly detecting the positions of the active markers 66 on the active marker plate 65 by a 3-D position sensor.

While an active marker plate 65 is used in the above description, the active markers 66 do not necessarily have to be placed on an active marker plate 65.

For example, it may alternatively be so arranged that the active markers 66 can be directly driven into the reference frame 1 like so man! screws. If such is the case, the positions of the active markers can be reliably defined on the reference frame 1 so that the positions of the primary markers 5 through 11 on the reference frame 1 can be computationally determined in terms of the coordinate system 30 for the real space without detecting them on the reference frame 1 by mean of a probe in a manner as described above.

Figure 27:
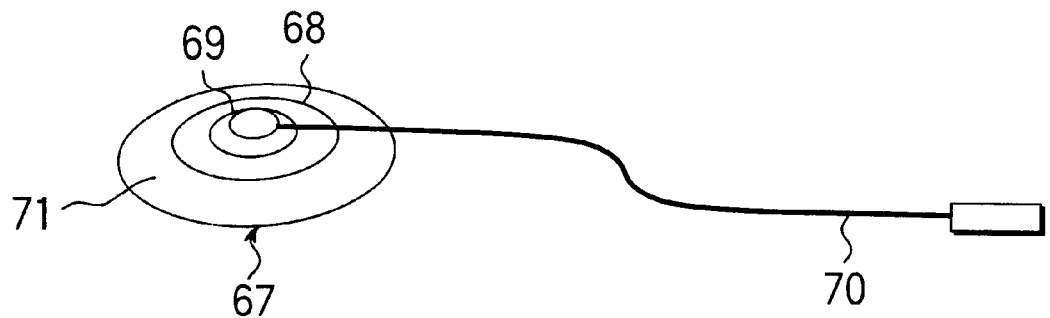
FIG. 27 is a schematic perspective view of an active secondary marker that can be used with the sixth embodiment, illustrating the configuration thereof.

FIG. 27 is a schematic perspective view of an active secondary marker 67 that can be used with the sixth embodiment, illustrating the configuration thereof. As shown in FIG. 27, an LED section 69 that is an IR LED sensor is fitted to the main body 68 of the active secondary marker 67 and, as the IR LED section 69 emits IRs, the three-dimensional position of the IR LED section 69 and hence that of the active secondary marker 67 can be detected in terms of the coordinate system 30 for the real space by a 3-D sensor 28. The emission of IRs of the LED section 69 is controlled by a control unit (e.g., PC 25) connected to the active secondary marker 67 by way of an LED wiring section 60.

The active secondary marker 67 is secured to the surface of the body of the subject 27 by the adherent section 71 of the marker 67.

Figure 28:
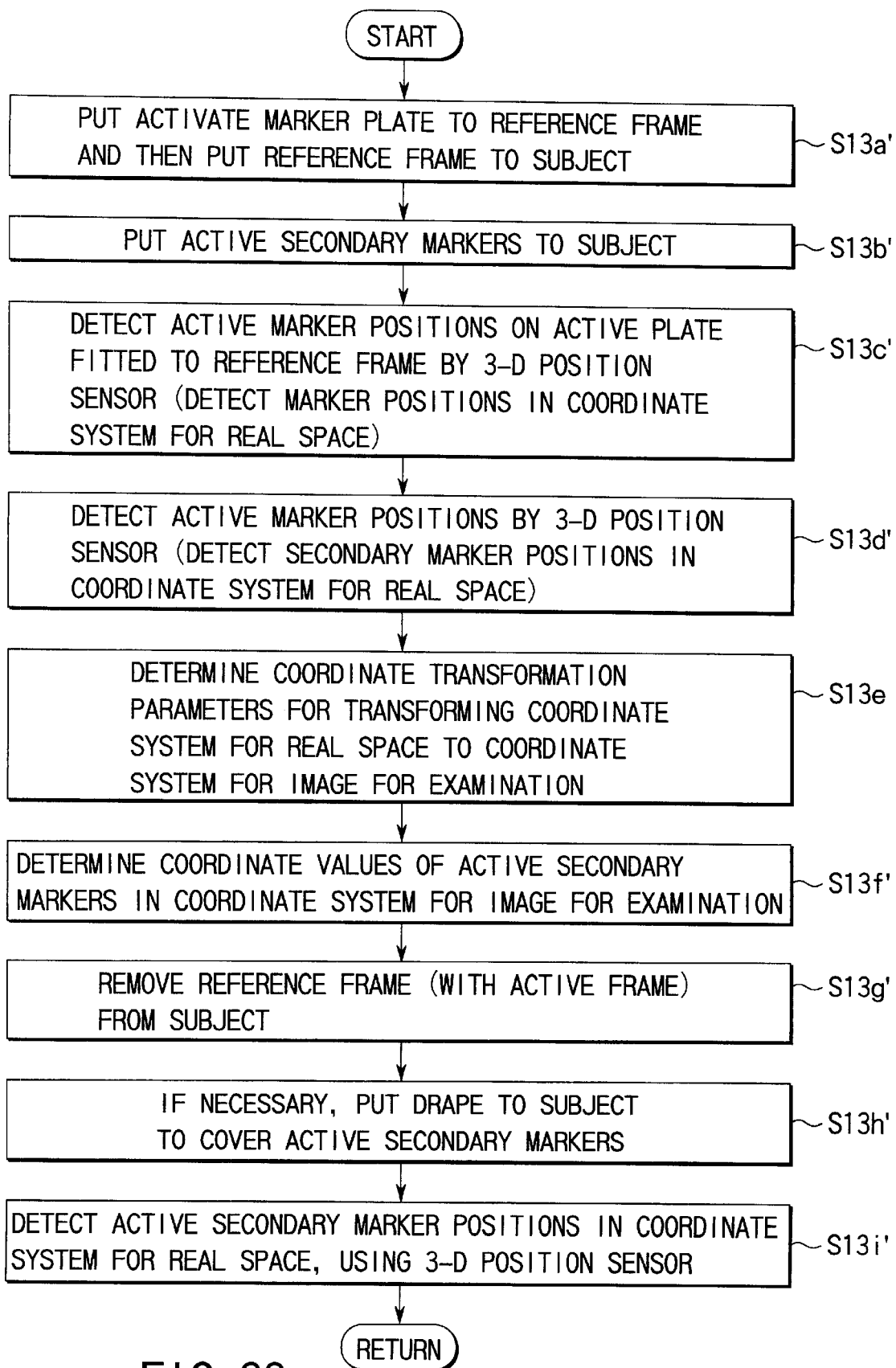
FIG. 28 is a flow chart of the step of detecting a marker in a real space containing a subject of examination in FIG. 13 when conducted by using the sixth embodiment of the invention.

With the sixth embodiment, the processing operation of Step S13 proceeds in at manner as described below by referring to FIG. 28.

Firstly, the active marker plate 65 is fitted to the reference frame 1 (Step S13a') Then, the reference frame 1 is fitted to the subject 27 (with the active marker plate). At this time, it is necessary to make sure that the reference frame 1 is fitted to the subject 27 at the same position where it is fitted when tomographic images of the subject 27 are taken for medical examination. As described earlier by referring to the fourth embodiment, filling materials 18, 19 that harden with time may effectively be used to securely place the reference frame 1 in position.

Thereafter, active secondary markers 67 are fitted to the body of the subject 27 (Step S13b') at respective positions on the surface of the subject that can be effectively detected by the 3-D position sensor 24 during the surgical operation as shown in FIG. 22. The number of active secondary markers 67 to be fitted to the body of the subject 27 should be three or greater than three.

Then, the positions of the active secondary markers 67 on the active marker plate 65 are detected by the 3-D position sensor 24 and then the coordinate values of the primary markers on the reference frame 1 are determined in terms of the coordinate system 30 for the real space (Step S13c'). The technique used for determining the coordinate values is already described and hence will not be described here any further. Assume that the coordinates of the primary markers are $(X_W(i), Y_W(i), Z_W(i))$.

Subsequently, the positions of the active secondary markers 67 are detected by the electrode position sensor 24 and their coordinate values in the coordinate system 30 for the real space are determined (Step S13d'). Assume that the coordinates of the active secondary markers 67 are $(X_{W2}(J), Y_{W2}(J), Z_{W2}(J))$.

Then, the coordinate transformation parameters for transforming the coordinate system 30 for the real space into the coordinate system 29 for the image for examination are determined (Step S13e). More specifically, the coordinate transformation parameters $_PH_W$ for transforming the coordinate system 30 for the real space into the coordinate system 29 for the image for examination are determined by using the coordinate pairs $(X_P(k), Y_P(k), Z_P(k))$, $(X_W(k), Y_W(k), Z_W(k))$ for the positions of the primary markers detected on the reference frame 1 by way of both the coordinate system 30 for the real space and the coordinate system 29 for the image for examination.

Thereafter, the coordinate values of the positions of the active secondary markers 67 in the coordinate system 29 for the image for examination are determined (Step S13f') and are registered for the active secondary markers 67 by utilizing the coordinate transformation parameters $_PH_W$ for transforming the coordinate system 30 for the real space into the coordinate system 29 for the image for examination as determined in Step S13e. In mathematical terms, the coordinate values $(X_{P2}(J), Y_{P2}(J), Z_{P2}(J))$ of the active secondary markers 67 in the coordinate system 29 for the image for examination are computationally determined by using the equation below.

$$\begin{bmatrix} x_{P2}(j) \\ y_{P2}(j) \\ z_{P2}(j) \\ 1 \end{bmatrix} = {}_PH_W \begin{bmatrix} x_{W2}(j) \\ y_{W2}(j) \\ z_{W2}(j) \\ 1 \end{bmatrix}$$

Subsequently, the reference frame 1 is removed from the body of the subject 27 (with the active marker plate) (Step S13g'). Note, however, the active secondary markers 67 are not removed in this step.

Thereafter, if necessary, a drape is put on the subject 27 who is still carrying the active secondary markers 67 in order to produce a clean environment necessary for the surgical operation in the operating room (Step S13h').

Then, the positions of the active secondary markers 67 in the coordinate system 30 for the real space are detected by the 3-D position sensor 24 (Step S13i'). Assume that the coordinates of the active secondary markers are expressed by $(X_{W2}(J), Y_{W2}(J), Z_{W2}(J))$.

Thus, the positions of the active secondary markers 67 can be three-dimensionally detected in terms of the coordinate system 30 for the real space in Step S13.

Then, the coordinates of the coordinate system 29 for the image for examination and those of the coordinate system 30 for the real space are registered as described above in Step S14 of the fourth embodiment and that of the fifth embodiment.

As described above, with the sixth embodiment, the opening of operative calibration can be conducted efficiently without the need of detecting the secondary markers by a sensor probe.

Thus, any errors due to the use of a sensor probe can be eliminated to improve the accuracy of operative calibration.

With the sixth embodiment, the markers are provided with the role of a sensor so that the cumbersome of operation required for calibration can be eliminated during the surgical operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical operation navigating system comprising:
a reference frame being fitted to a subject of medical treatment in a tomographic image of the subject by using three spots on the surface of the body of the subject, which include at least one of the top of the left ear, the top of the right ear and the nasal projection, and having three or more than three markers detectable at least either in an X-ray image or in an MRI image thereof, said markers being arranged at predetermined positions constituting a plane;
a coordinate computing section for computationally determining the coordinates of the markers on the reference frame in terms of a coordinate system uniquely defined for the image for examination; and
a correspondence computing section for computationally determining the transformation between said coordinate system for the tomographic image for examination and a coordinate system defined for the real space containing said markers on the basis of the coordinates of the markers as determined by said coordinate computing section in terms of the coordinate system for the tomographic image for examination and the coordinates of the markers as determined in terms of said coordinate system for the real space.

2. A surgical operation navigating system comprising:
a reference frame being fitted to a subject of medical treatment in a tomographic image of the subject by using three spots on the surface of the body of the subject, which include at least one of the top of the left ear, the top of the right ear and the nasal projection, and having three or more than three markers detectable at least either in an X-ray image or in an MRI image thereof, said markers being arranged at predetermined positions constituting a plane;
a coordinate computing section for computationally determining the coordinates of the markers on the reference frame in terms of a coordinate system uniquely defined for the image for examination;
a first correspondence computing section for computationally determining the transformation between said coordinate system for the tomographic image for examination and a coordinate system defined for the real space containing said markers on the basis of the output of said coordinate computing section and the coordinates of the markers as determined in terms of said coordinate system for the real space;
a second correspondence computing section for computationally determining the transformation between said coordinate system for the real space and a coordinate system uniquely defined for a surgical instrument on the basis of the coordinates of the surgical instrument as determined in terms of the coordinate system for the real space; and
a third correspondence computing section for computationally determining the transformation between said coordinate system for the tomographic image for examination and said coordinate system for the surgical instrument on the basis of the outputs of said first and second correspondence computing sections.

3. A surgical operation navigating system according to claim 2, further comprising:
a display section adapted to display a plurality of images obtained from different view angles to show the positional relationship of the subject, a target and the surgical instrument on the basis of the outputs of said first through third correspondence computing section.

4. A surgical operation navigating system according to claim 2, further comprising:
a display section adapted to display an image obtained from a view angle directed along the surgical instrument on the basis of the outputs of said first through third correspondence computing section.

5. A surgical operation navigating system comprising:
a reference frame being fitted to a subject of medical treatment in a tomographic image of the subject by using three spots on the surface of the body of the subject, which include at least one of the top of the left ear, the top of the right ear and the nasal projection, and having three or more than three markers detectable at least either in an X-ray image or in an MRI image thereof, said markers being arranged at predetermined positions constituting a plane,
a second reference frame being relatively fitted to said subject;
a coordinate computing section for computationally determining the coordinates of the markers on the first reference frame in terms of a coordinate system uniquely defined for the image for examination;
a correspondence computing section for computationally determining the transformation between said coordinate system for the image for examination and a coordinate system defined for the real space containing said markers on the first reference frame on the basis of the output of said coordinate computing section and the coordinates of the markers on the first reference frame as determined in terms of said coordinate system for the real space; and
a correcting section for correcting the result of said correspondence computing section on the basis of the coordinates of the second reference frame as determined during a surgical operation in terms of said coordinate system for the real space.

6. A surgical operation navigating system according to claim 5, wherein said second reference frame is removably fitted to said first reference frame.

7. A surgical operation navigating system according to claim 5, wherein said second reference frame is provided with a plurality of markers that are IR emitting diodes.

8. A surgical operation navigating system according to claim 7, wherein said second reference frame is removably fitted to said first reference frame.

9. A surgical operation navigating system comprising:
a reference frame adapted to be rigidly anchored to a subject of medical treatment by utilizing three spots on the surface of the body of the subject, which include at least one of the top of the left ear, the top of the right ear and the nasal projection, and to carry at least three markers thereon at positions constituting a plane, said markers containing a material adapted to make them detectable at least either in an X-ray image or an MRI image of the frame; and an image acquisition section for acquiring, tomographic images of the subject for medical examination with the reference frame;

a marker position detecting section for detecting the positions of the markers in terms of the coordinate system for the tomographic image for examination;

a marker detecting section for detecting the markers on the frame fitted to the subject in the real space; and a registering section for registering the coordinates of the tomographic image for examination and those of the subject by registering the coordinates of the marker positions as detected by said marker position detecting section and the coordinates of the markers as detected by said marker detecting section.

10. A surgical operation navigating system according to claim 9, wherein at least the tops of the left and right ears and the nasal projection are selected for said three spots on the surface of the body of the subject.

11. A surgical operation navigating system according to claim 9, wherein said reference frame is positionally regulated by a material that hardens with time before rigidly anchoring said reference frame to the subject by utilizing the three spots on the surface of the body of the subject.

12. A surgical operation navigating system according to claim 9, wherein said marker detecting section registers the coordinates of the image for examination and the body of the subject as it probes and detects the markers by a 3-D position sensor when detecting the markers of the reference frame in the real space.

13. A surgical operation navigating system according to claim 12, wherein said 3-D position sensor is an optical sensor system adapted to detect infrared rays.

14. A surgical operation navigating system according to claim 12, wherein said reference frame is fitted to the subject, one of a iodine-containing type drape, a transparent drape and a translucent drape is placed on the subject and then said 3-D position sensor probes the markers on the reference frame from above the drape.

15. A surgical operation navigating system according to claim 12, wherein the reference frame and a secondary marker plate are fitted to the subject, the coordinates of the reference frame and those of the secondary marker plate are registered and subsequently the relative positions of the subject and the surgical instrument are defined by defining the positions of secondary markers and detecting the relative positions of the secondary marker plate and the surgical instrument by said 3-D position sensor.

16. A surgical operation navigating system according to claim 15, wherein said markers have a substantially cylindrical profile and the tops thereof defined as marker positions.

17. A surgical operation navigating system according to claim 15, wherein either said markers are or said secondary marker plate is removable.

18. A surgical operation navigating system according to claim 9, wherein said markers have one of a conical profile, a truncated cone profile and a conical recess, when said markers have one of the conical profile and the truncated cone profile, the tops of said markers are defined as marker positions, and when said markers have the conical recess, the bottoms of the recesses are defined as marker positions.

19. A surgical operation navigating system according to claim 9, wherein said marker position detecting section recognizes the profiles of the markers in the image of for examination and detects the marker positions from the profiles of the markers.

20. A reference frame comprising:

a fitting section for fitting the reference frame with a subject of medical treatment at least three spots on the surface of a body of the subject, one of the three spots including one of the top of the left ear, the top of the right ear and the nasal projection; and markers formed by combining a material easily detectable in an image of a first examining method and a material easily detectable in an image of a second examining method.

21. A reference frame according to claim 20, wherein said first and second examining methods utilizes X-rays and MRI respectively.

22. A calibration method for computing positional and orientational transformation between a subject of medical treatment and a tomographic image of the subject by using the corresponding relationship between the coordinates of a reference frame fitted to the subject in the image and the coordinates of the reference frame in the real space, said method comprising steps of:

anchoring said reference frame to the subject of medical treatment by using three spots on the surface of the body of the subject, one of the three spots including one of the top of the left ear, the top of the right ear and the nasal projection;

fitting markers other than said reference frame to said subject;

determining the coordinates of said markers in said image by using the coordinates of the markers in the real space and said corresponding relationship; and computing positional and orientational transformation between said subject and the image of said subject by using the determined coordinates of the markers.

23. A calibration method according to claim 22, wherein said markers are plural in number and only the markers having errors found within a predetermined range as detected in the real space are used to compute positional and orientational transformation between said subject and the image of said subject.

24. A calibration apparatus for computing positional and orientational transformation between a patient to be subjected to a surgical operation and a tomographic image of the patient by using the corresponding relationship between the coordinates of a reference frame fitted to the patient in the image and the coordinates of the reference frame in the real space, said apparatus comprising:

an anchoring mechanism for anchoring said reference frame to the patient by using three spots on the surface of the body of the patient one of the three spots including one of the top of the left ear, the top of the right ear and the nasal projection;

markers fitted to the patient other than the reference frame;

a coordinate detecting section for determining the coordinates of said markers on said image by using the coordinates of the markers in the real space and said corresponding relationship; and a registering section for computing positional and orientational transformation between said patient and the image of said patient by using the coordinates of the markers determined by said coordinate detecting section.

25. A calibration apparatus according to claim 24, wherein said markers are plural in number and only the markers having errors found within a predetermined range as detected in the real space are used to compute positional and orientational transformation between said patient and the image of said patient.

26. A calibration method for computing positional and orientational transformation between a subject of medical treatment and a tomographic image of the subject by using the corresponding relationship between the coordinates of a reference frame fitted to the subject in the image and the coordinates of the reference frame in the real space, said method comprising steps of:

anchoring the reference frame to the patient by using three spots on the surface on the body of the subject, one of the three spots including one of the top of the left ear, the top of the right ear and the nasal projection;

fitting markers other than said reference frame to said subject;

determining the coordinates of said markers on said image by using the coordinates of the markers in the real space and said corresponding relationship; and computing positional and orientational transformation between said subject and the image of said subject by using said markers.

27. A calibration method according to claim 26, wherein said markers have respective position detecting sensors.

28. A calibration method according to claim 26, wherein said markers are plural in number and only the markers having errors found within a predetermined range as detected in the real space are used to compute positional and orientational transformation between said subject and the image of said subject.

29. A calibration method according to claim 28, wherein said markers have respective position detecting sensors.

30. A method of computing positional and orientational transformation between a subject of medical treatment and a tomographic image of said subject, said method comprising steps of:

fitting a reference frame adapted to be removably placed on the subject by using three spots on the surface of the body of the subject, one of the three spots including one of the top of the left ear, the top of the right ear and the nasal projection, said reference frame being provided thereon with a plurality of first markers;

taking a tomographic image of the subject carrying said reference frame thereon and determining the coordinates of the markers appearing in the image of said subject in terms of a coordinate system defined for said image;

fitting a plurality of second markers to the subject carrying said reference frame and determining the coordinates of the first markers and those of the second markers in terms of a coordinate system defined for the real space;

computing the positional and orientational transformation between the coordinate system defined for the real space and the coordinate system defined for said image on the basis of the coordinates of said first markers in the coordinate system defined for the real space and those of said first markers in the coordinate system defined for the image;

determining the coordinates of said second markers in the coordinate system defined for said image by using the coordinates of said second markers in the coordinate system defined for said real space and said positional and orientational transformation; and computing positional and orientational transformation between said subject and the image of said subject by using the coordinates of said second markers.

31. An operative calibration apparatus of computing positional and orientational transformation between a patient to be subjected to a surgical operation and a tomographic image of said patient, said apparatus comprising:

a reference frame to be fitted to the patient by using three spots on the surface of the body of the subject, one of the three spots including one of the top of the left ear, the top of the right ear and the nasal projection, said reference frame being adapted to be removably placed on the patient and provided thereon with a plurality of first markers;

a first detecting section for taking a tomographic image of the patient carrying said reference frame thereon and determining the coordinates of the markers appearing in the image of said patient in terms of a coordinate system defined for said image;

a second detecting section for detecting it plurality of second markers to be fitted to the patient carrying said reference frame and determining the coordinates of the first markers and those of the second markers in terms of a coordinate system defined for the real space;

a relationship computing section for computing the positional and orientational transformation between the coordinate system defined for the real space and the coordinate system defined for said image on the basis of the coordinates of said first markers in the coordinate system defined for the real space determined by said first detecting section and those of said first markers in the coordinate system defined for the image;

a coordinate computing section for determining the coordinates of said second markers in the coordinate system defined for said image by using the coordinates of said second markers in the coordinate system defined for said real space determined by said second detecting section and said positional and orientational transformation determined by said relationship computing section; and a registering section for computing positional and orientational transformation between said patient and the image of said patient by using the coordinates of said second markers determined by said coordinate computing section.

32. A calibration method of calibrating the position and orientation of a subject of medical treatment and a tomographic image of the subject by using a reference frame securely fitted to the subject, said method comprising steps of:

securely fitting the reference frame to the subject by using three spots on the surface of the body of the subject, one of the three spots including one of the top of the left ear, the top of the right ear and the nasal projection;

fitting markers to said subject, said mark being located at a different position from the position of the reference frame;

defining the positions of said markers in a coordinate system for the image for examination as defined for the image for examination by, using said reference frame; and registering the coordinates of said coordinate system for the image for examination and the coordinate system for the real space by detecting the positions of said markers in the coordinate system for the real space as defined for the real space containing said subject.

33. A calibration method according to claim 32, wherein the values of the detected positions of the markers having errors exceeding a predetermined value are eliminated when registering the coordinates of said coordinate system for the image for examination and the coordinate system for the real space.

34. A calibration method according to claim 33, wherein said markers have respective position detecting sensors.

35. A calibration apparatus of calibrating the position and orientation of a patient to be subjected to a surgical operation and a tomographic image of the patient by using a reference frame securely fitted to the subject, said apparatus comprising:
   a fitting mechanism for securely fitting the reference frame to the patient by using three spots on the surface of the body of the patient, one of the three spots including one of the top of the left ear, the top of the right ear and the nasal projection;
   markers being located at a different position from the position of said reference frame and being adapted to be fitted to said patient;
   a position defining section for defining the positions of said markers in a coordinate system for the image for examination as defined for the image for examination by using said reference frame; and
   an registering section for registering the coordinates of said coordinate system for the image for examination and the coordinate system for the real space by detecting the positions of said markers in the coordinate system for the real space as defined for the real space containing said patient.

36. A calibration apparatus according to claim 35, wherein said registering section eliminates the values of the detected positions of the markers having errors exceeding a predetermined when registering the coordinates of said coordinate system for the image for examination and the coordinate system for the real space.

37. A calibration method according to claim 35, wherein said markers have respective position detecting sensors.

38. A surgical operation navigating system comprising:
   a reference means being fitted to a subject of medical treatment in a tomographic image of the subject by using three spots on the surface of the body of the subject, which include at least one of the top of the left ear, the top of the right ear and the nasal projection having three or more than three markers detectable at least either in an X-ray image or in an MRI image thereof, said markers being arranged at predetermined positions constituting a plane;
   a coordinate computing means for computationally determining the coordinates of the markers on the reference means in terms of a coordinate system uniquely defined for the image for examination; and
   a correspondence computing means for computationally determining the transformation between said coordinate system for the image for examination and a coordinate system defined for the real space containing said markers on the basis of the coordinates of the markers as determined by said coordinate computing means in terms of the coordinate system for the tomographic image for examination and the coordinates of the markers as determined in terms of said coordinate system for the real space.

39. A surgical operation navigating system comprising:
   a reference means being fitted to a subject of medical treatment in a tomographic image of the subject by using three spots on the surface of the body of the subject, which include at least one of the top of the left ear, the top of the right ear and the nasal projection having three or more than three markers detectable at least either in an X-ray image or in an MRI image thereof, said markers being arranged at predetermined positions constituting a plane;
   a coordinate computing means for computationally determining the coordinates of the markers on the reference means in terms of a coordinate system uniquely defined for the image for examination;
   a first correspondence computing means for computationally determining the transformation between said coordinate system for the tomographic image for examination and a coordinate system defined for the real space containing said markers on the basis of the output of said coordinate computing means and the coordinates of the markers as determined in terms of said coordinate system for the real space;
   a second correspondence computing means for computationally determining the transformation between said coordinate system for the real space and a coordinate system uniquely defined for a surgical instrument on the basis of the coordinates of the surgical instrument as determined in terms of the coordinate system for the real space; and
   a third correspondence computing means for computationally determining the transformation between said coordinate system for the image for examination and said coordinate system for the surgical instrument on the basis of the outputs of said first and second correspondence computing means.

40. A surgical operation navigating system comprising:
   a reference means being fitted to a subject of medical treatment in a tomographic image of the subject by using three spots on the surface of the body of the subject, which include at least one of the top of the left ear, the top of the right ear and the nasal projection having three or more than three markers detectable at least either in an X-ray image or in an MRI image thereof, said markers being arranged at predetermined positions constituting a plane,
   a second reference means being relatively fitted to said subject;
   a coordinate computing means for computationally determining the coordinates of the markers on the first reference means in terms of a coordinate system uniquely defined for the tomographic image for examination;
   a correspondence computing means for computationally determining the transformation between said coordinate system for the tomographic image for examination and a coordinate system defined for the real space containing said markers on the first reference means on the basis of the output of said coordinate computing means and the coordinates of the markers on the first reference means as determined in terms of said coordinate system for the real space; and
   a correcting means for correcting the result of said correspondence computing means on the basis of the coordinates of the second reference means as determined during a surgical operation in terms of said coordinate system for the real space.

41. A surgical operation navigating system comprising:

a reference means adapted to be rigidly anchored to a subject of medical treatment by utilizing three spots on the surface of the body of the subject, which include at least one of the top of the left ear, the top of the right ear and the nasal projection to carry at least three markers thereon at positions constituting a plane, said markers containing a material adapted to make them detectable at least either in an X-ray image or an MRI image of the frame; and an image acquisition means for acquiring, images of the subject for medical examination with the reference means;

a marker position detecting mans for detecting the positions of the markers in terms of the coordinate system for the image for examination;

a marker detecting means for detecting the markers on the frame fitted to the subject in the real space; and a registering means for registering the coordinates of the image for examination and those of the subject by registering the coordinates of the marker positions as detected by said marker position detecting means and the coordinates of the markers as detected by said marker detecting means.

42. A calibration apparatus for computing positional and orientational transformation between a patient to be subjected to a surgical operation and a tomographic image of the patient by using the corresponding relationship between the coordinates of a reference means fitted to the patient in the image and the coordinates of the reference means in the real space, said apparatus comprising:

an anchoring means for anchoring said reference means to the patient by using three spots on the surface of the body of the patient, one of the three spots including one of the top of the left ear, the top of the right ear and the nasal projection;

markers fitted to the patient other than the reference means;

a coordinate detecting means for determining the coordinates of said markers on said image by using the coordinates of the markers in the real space and said corresponding relationship; and a registering means for computing positional and orientational transformation between said patient and the image of said patient by using the coordinates of the markers determined by said coordinate detecting means.

43. An operative calibration apparatus of computing positional and orientational transformation between a patient to be subjected to a surgical operation and a tomographic image of said patient, said apparatus comprising:

a reference means to be fitted to the patient by using three spots on the surface of the body of the subject, one of the three spots including one of the top of the left ear, the top of the right ear and the nasal projection, said reference means being adapted to be removably placed on the patient and provided thereon with a plurality of first markers;

a first detecting means for taking a tomographic image of the patient carrying said reference means thereon and determining the coordinates of the markers appearing in the image of said patient in terms of a coordinate system defined for said image;

a second detecting means for detecting a plurality of second markers to be fitted to the patient carrying said reference means and determining the coordinates of the first markers and those of the second markers in terms of a coordinate system defined for the real space;

a relationship computing means for computing the positional and orientational transformation between the coordinate system defined for the real space and the coordinate system defined for said image on the basis of the coordinates of said first markers in the coordinate system defined for the real space determined by said first detecting means and those of said first markers in the coordinate system defined for the image;

a coordinate computing means for determining the coordinates of said second markers in the coordinate system defined for said image by using the coordinates of said second markers in the coordinate system defined for said real space determined by said second detecting means and said positional and orientational transformation determined by said relationship computing means; and a registering means for computing positional and orientational transformation between said patient and the image of said patient by using the coordinates of said second markers determined by said coordinate computing means.

44. A calibration apparatus of calibrating the position and orientation of a patient to be subjected to a surgical operation and a tomographic image of the subject by using a reference means securely fitted to the subject, said apparatus comprising:

a fitting means for securely fitting the reference means to the patient by using three spots on the surface of the body of the patient, one of the three spots including one of the top of the left ear, the top of the right ear and the nasal projection; and markers being located at a different position from the position of said reference means and being adapted to be fitted to said patient;

a position defining means for defining the positions of said markers in a coordinate system for the image for examination as defined for the image for examination by using said reference means; and a registering section for registering the coordinates of said coordinate system for the image for examination and the coordinate system for the real space by detecting the positions of said markers in the coordinate system for the real space as defined for the real space containing said patient.

* * * * *